United States Patent [19]

Hamanaka

[11] Patent Number: 4,619,924

[45] Date of Patent: Oct. 28, 1986

[54] 2-ALKYLTHIOPENEM DERIVATIVES

[75] Inventor: Ernest S. Hamanaka, Gales Ferry, Conn.

[73] Assignee: Pfizer Inc., New York, N.Y.

[21] Appl. No.: 675,258

[22] Filed: Nov. 27, 1984

Related U.S. Application Data

[63] Continuation-in-part of Ser. No. 610,916, May 18, 1984, abandoned, which is a continuation-in-part of Ser. No. 506,475, Jun. 21, 1983, abandoned.

[51] Int. Cl.$^4$ .................. C07D 499/00; A61K 31/425
[52] U.S. Cl. ..................................... 514/195; 514/192; 540/310
[58] Field of Search ................. 260/245.2 R, 245.2 T; 514/192, 195

[56] References Cited

U.S. PATENT DOCUMENTS 4,395,418  7/1983  Ohki et al. ......................... 424/270
4,431,654  2/1984  Girijavallabhan et al. ......... 424/270

FOREIGN PATENT DOCUMENTS 58-43978  3/1983  Japan .

Primary Examiner—Nicholas S. Rizzo
Attorney, Agent, or Firm—Charles J. Knuth; Peter C. Richardson; J. Trevor Lumb

[57] ABSTRACT

Certain 2-alkylthio-2-penem-3-carboxylic acid compounds are useful as antibacterials for treating mammals.

24 Claims, No Drawings

2-ALKYLTHIOPENEM DERIVATIVES

This application is a continuation-in-part of Ser. No. 610,916, filed May 18, 1984, now abandoned, which is a continuation-in-part of Ser. No. 506,475, filed June 21, 1983, now abandoned.

BACKGROUND OF THE INVENTION

This invention is directed to a family of anti-bacterial agents incorporating a 2-azetidinone (beta-lactam) ring. Chemically, the antibacterial agents of this invention are identified as 6-alpha-hydroxethyl-2-substituted-2-penem-3-carboxylic acid compounds.

Although certain 2-substituted-2-penem-3-carboxylic acid compounds have been previously disclosed, there is a continuing need for novel compounds having desirable antibacterial therapeutic properties.

SUMMARY OF THE INVENTION

The present inventions is directed to a compound of the formula

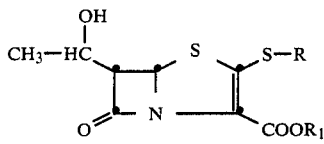

or a pharmaceutically acceptable salt thereof, wherein:
R is 2-(methylsulfinyl)ethyl, 2-(methylsulfonyl)ethyl, (methylsulfinyl)methyl, (methylsulfonyl)methyl, 2-thiolanyl, 1-oxo-2-thiolanyl, 3-thiolanyl, 1-oxo-3-thiolanyl, 1,1-dioxo-3-thiolanyl, 3-thianyl, 1-oxo-3-thianyl, 1,1-dioxo-3-thianyl, 3-oxo-perhydro-1,4-thiazin-2-yl, 4-formyl-perhydro-1,4-thiazin- 2-yl, 4-oxo-1,4-oxathian-3-yl, 4,4-dioxo-1,4-oxathian-3-yl, 1,3-dithiolan-2-yl, 1,2-dithiolan-4-yl, (2-methyl-3,3-dioxo-1,3-oxathiolan-5-yl)methyl, 3-thietanyl, 1-oxo-3-thietanyl or 1,1-dioxo-3-thietanyl, and $R_1$ is hydrogen or a group which forms an ester which is hydrolyzed in vivo.

Preferred compounds include those wherein R is 2-(methylsulfinyl)ethyl, 2-(methylsulfonyl)ethyl, (methylsulfinyl)methyl, (methylsulfonyl)methyl, 3-thietanyl, 1-oxo-3-thietanyl, 1,1-dioxo-3-thietanyl, 3-thiolanyl, 1-oxo-3-thiolanyl, 1,1-dioxo-3-thiolanyl, 3-hydroxy-4-thianyl, 1-oxo-3-hydroxy-4-thianyl, 1,1-dioxo-3-hydroxy-4-thianyl, 3-thianyl, 1-oxo-3-thianyl, 1,1-dioxo-3-thianyl, 4-thianyl, 1-oxo-4-thianyl, 1,1-dioxo-4-thianyl, or 2-oxo-1,3-dithiolan-4-yl-methyl.

Particularly preferred compounds include those wherein R is 1-oxo-3-thiolanyl, 1,1-dioxo-3-thiolanyl, 1-oxo-3-thietanyl, 1-oxo-3-thianyl, 1,1-dioxo-4-thianyl, 4-thianyl.

Included within the scope of the present invention is a compound of the formula

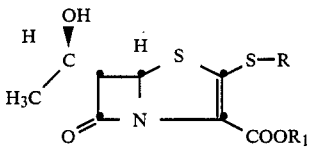

or a pharmaceutically acceptable salt thereof, wherein:
R and $R_1$ are as defined above for compounds of formula I.

Preferred compounds include those wherein R is as described as preferred for compounds of formula I.

Particularly preferred compounds include those of formula II wherein R is cis or trans-1-oxo-3-thiolanyl, 1,1-dioxo-3-thiolanyl, cis-or trans-1-oxo-3-thietanyl, cis- or trans-1-oxo-3-thianyl, 1,1-dioxo-4-thianyl, 4-thianyl, or cis- or trans-1-oxo-4-thianyl.

Further embraced by the present invention is a pharmaceutical composition comprising a compound of formula I or II and a pharmaceutically acceptable diluent or carrier; and a method of treating a bacterial infection in a mammal comprising administering an antibacterially effective amount of a compound of formula I or II.

DETAILED DESCRIPTION OF THE INVENTION

The compounds of formulas I and II are useful as antibacterial agents, and are derivatives of the bicyclic nucleus of the formula:

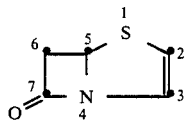

Throughout this specification, the nucleus of formula III is identified by the name "2-penem," and ring atoms are numbered as shown. The carbon atom attached to ring carbon 6 is given the number 8. Also, throughout this specification, the abbreviation "PNB" is used for the p-nitrobenzyl group.

The relationship between the hydrogen on bridgehead carbon 5 and the remaining hydrogen on carbon 6 in compounds of formula I can either be cis or trans. The present invention embraces both isomers as well as mixtures thereof. The trans isomer is generally preferred in pharmaceutical applications and the cis isomer can be readily converted to the trans-isomer.

Generally, carbon 5 will have the absolute stereochemistry designated R using the Prelog-Ingold R,S stereochemical notation, which is employed in this application. Thus, for example, a compound of formula II where in $R_1$ is hydrogen and R is 4-thianyl is named (5R, 6S)-6-[(R)-1-hydroxyethyl]-2-(4-thianyl)thio-3-carboxyl-2-penem.

As will be appreciated, various optically active isomers of the new compounds are possible. The present invention embraces such optically active isomers as well as mixtures thereof.

The present invention is directed to penems substituted in the 2-position by a moiety of the general formula R—S—. Useful compounds include those wherein R is any of a number of alkyl derivatives. For example, R can be a group having the formula $(alk_1)S(O)_i(alk_2)—$ wherein $alk_1$ is alkyl having 1–4 carbon atoms, $alk_2$ is alkylene having 1–6 carbon atoms, preferably branched adjacent to the sulfur atom linked to the 2-penem, and i is zero, 1 or 2.

Also, R can be a group of the formula

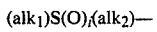

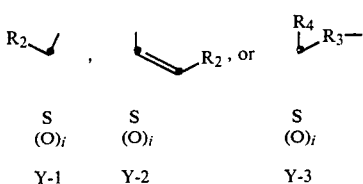

wherein Y-1, Y-2 and Y-3 are cyclic moieties containing 3-7 carbon atoms or wherein one of the carbon atoms is replaced by $R_5$—N wherein $R_5$ is alkylcarbonyl having 1-4 carbon atoms, formyl or alkylsulfonyl having 1-4 carbon atoms, oxygen or $S(O)_j$, j=0, 1 or 2, $R_2$ and $R_4$ are hydrogen or alkyl having 1-4 carbon atoms and $R_3$ is alkylene having 1-6, carbon atoms. Y-1 and Y-3 can have unsaturation in the ring. The ring carbon atoms comprising the cyclic moieties Y-1, Y-2 and Y-3 can have a substituent which is oxo, alkyl having 1-4 carbon atoms, alkoxy having 1-4 carbon atoms, alkyl $S(O)_j$ having 1-4 carbon atoms, cyano, amino, N-alkylamino having 1-4 carbon atoms, N,N-dialkylamino wherein each alkyl has 1-4 carbon atoms, halo, alkylcarbonylamino having 1-5 carbon atoms, hydroxyl, carboxyl, aminocarbonyl, N-alkylaminocarbonyl or N,N-dialkylaminocarbonyl.

The alkyl or alkylene groups of $alk_1$, $alk_2$, $R_2$, $R_3$ or $R_4$ can be unsubstituted or substituted by aryl, aralkyl, heterocyclyl, alkoxy, alkyl $S(O)_i$, cyano, amino, N-alkylamino having 1-4 carbon atoms, N,N-dialkylamino wherein each alkyl has 1-4 carbon atoms, halo, alkylcarbonylamino having 2-5 carbon atoms, hydroxyl, alkylsulfonylamino having 1-4 carbon atoms, carboxyl, aminocarbonyl, N-alkylaminocarbonyl having 1-4 carbon atoms or N,N-dialkylaminocarbonyl wherein each alkyl has 1-4 carbon atoms.

Compounds may include those wherein R is 2-(methylsulfinyl)ethyl, 2-(methylsulfonyl)ethyl, (methylsulfinyl)methyl, (methylsulfonyl)methyl, 2-(ethylsulfinyl)ethyl, 2-(ethylsulfonyl)ethyl, 1-(methylsulfinyl)ethyl, 1-(methylsulfonyl)ethyl, 3-thietanyl, 1-oxo-3-thietanyl, 1,1-dioxo-3-thietanyl, 3-thiolanyl, 1-oxo-3-thiolanyl, 1,1-dioxo-3-thiolanyl, 4-methyl-3-thiolanyl, 4-methyl-1-oxo-3-thiolanyl, 4-methyl-1,1-dioxo-3-thiolanyl, 2-thiolanyl, 1-oxo-2-thiolanyl, 1,1-dioxo-2-thiolanyl, 2-thianyl, 1-oxo-2-thianyl, 1,1-dioxo-2-thianyl, 3-thianyl, 1-oxo-3-thianyl, 1,1-dioxo-3-thianyl, 4-thianyl, 1-oxo-4-thianyl, 1,1-dioxo-4-thianyl, 1,3-dithiolan-2-yl, 1-oxo-1,3-dithiolan-2-yl, 1,1-dioxo-1,3-dithiolan-2-yl, 1,3-dioxo-1,3-dithiolan-2-yl, 1,1,3-trioxo-1,3-dithiolan-2-yl, 1,1,3,3-tetraoxo-1,3-dithiolan-2-yl, 1,2-dithiolan-4-yl, 1-oxo-1,2-dithiolan-4-yl, (1,3-dithiolan-4-yl)methyl, (1,3-dioxo-1,3-dithiolan-4-yl)methyl, (1,1,3,3-tetraoxo-1,3-dithiolan-4-yl)methyl, (2-methyl-3-oxo-1,3-oxathiolan-5-yl)methyl, (2methyl-3,3-dioxo-1,3-oxathiolan-5-yl)methyl, 3-oxo-perhydro-1,4-thiazin-2-yl, 1,3-dioxo-perhydro-1,4-thiazin-2-yl, 1,1,3-trioxo-perhydro-1,4-thiazin-2-yl, 4-formyl-perhydro-1,4-thiazin-2-yl, 4-formyl-1-oxo-perhydro-1,4-thiazin-2-yl, 4-formyl-1,1-dioxo-perhydro-1,4-thiazin-2-yl, 1,4-oxathian-3-yl, 4-oxo-1,4-oxathian-3-yl, 4,4-dioxo-1,4-oxathian-3-yl, 1,3-dithian-2-yl, 1-oxo-1,3-dithian-2-yl, 1,1-dioxo-1,3-dithian-2-yl, 1,3-dioxo-1,3-dithian-2-yl, 1,1,3-trioxo-1,3-dithian-2-yl, 1,1,3,3-tetraoxo-1,3-dithian-2-yl, 1,3-dithian-5-yl, 1-oxo-1,3-dithian-5-yl, 1,3-dioxo-1,3-dithian-5-yl, 1,1,3,3-tetraoxo-1,3-dithian-5-yl, (1,3-oxathiolan-4-yl)methyl, (3-oxo-1,3-oxathiolan-4-yl)methyl, (3,3-dioxo-1,3-oxathiolan-4-yl)methyl), (1,3-oxathiolan-4-yl)(alkyl)methyl wherein alkyl has 1-4 carbon atoms, (3-oxo-1,3-oxathiolan-4-yl) (alkyl) methyl wherein alkyl has 1-4 carbon atoms, (3,3-dioxo-1,3-oxathiolan-4-yl)(alkyl)methyl wherein alkyl has 1-4 carbon atoms, (1,3-oxathiolan-5-yl)methyl, (3-oxo-1,3-oxathiolan-5-yl)methyl, (3,3-dioxo-1,3-oxathiolan-5-yl)methyl, (1,3-oxathiolan-5-yl) (alkyl)methyl wherein alkyl has 1-4 carbon atoms, (3-oxo-1,3-oxathiolan-5-yl)(alkyl) methyl wherein alkyl has 1-4 carbon atoms, (3,3-dioxo-1,3-oxathiolan-5-yl)(alkyl)methyl wherein alkyl has 1-4carbon atoms, 2-oxo-1,3-oxathian-5-yl, 2-oxo-perhydro-1,3-thiazin-5-yl, 3-alkyl-2-oxo-perhydro-1,3-thiazin-5-yl wherein alkyl has 1-4 carbon atoms, 1,4-oxathiepan-6-yl, 4-oxo-1,4-oxathiepan-6-yl, 4,4-dioxo-1,4-oxathiepan-6-yl, 1,4-dithiepan-6-yl, 1-oxo-1,4-dithiepan-6-yl, 1,1-dioxo-1,4-dithiepan-6-yl, 1,4-dioxo-1,4-dithiepan-6-yl, 1,1,4-trioxo-1,4-dithiepan-6-yl, 1,1,4,4-tetraoxo-1,4-dithiepan-6-yl, 1,4-thiazepan-6-yl, 1-oxo-1,4-thiazepan-6-yl, 1,1-dioxo-1,4-thiazepan-6-yl, 4-alkyl-1,4-thiazepan-6-yl wherein alkyl has 1-4 carbon atoms, 1-oxo-4-alkyl-1,4-thiazepan-6-yl wherein alkyl has 1-4 carbon atoms, 1,1-dioxo-4-alkyl-1,4-thiazepan-6-yl wherein alkyl has 1-4 carbon atoms, 4-alkanoyl-1,4-thiazepan-6-yl wherein alkanoyl has 1-5 carbon atoms, 4-alkanoyl-1-oxo-1,4-thiazepan-6-yl wherein alkanoyl has 1-5 carbon atoms, 4-alkanoyl-1,1-dioxo-1,4-thiazepan-6-yl wherein alkanoyl has 1-5 carbon atoms, 4-alkylsulfonyl-1,4-thiazepan-6-yl wherein alkyl has 1-4 carbon atoms, 4-alkylsulfonyl-1-oxo-1,4-thiazepan-6-yl, wherein alkyl has 1-4 carbon atoms, or 4-alkylsulfonyl-1,1-dioxo-1,4-thiazepan-6-yl wherein alkyl has 14 carbon atoms.

The present invention includes those penems in which the 3-carboxyl group is esterified with a non-toxic group ($R_1$) which is hydrolyzed in vivo. These esters are rapidly cleaved in mammalian blood or tissue to release the corresponding penem-3-carboxylic acid. Typical examples of such readily hydrolyzable ester-forming residues are alkanoyloxymethyl having from 3-8 carbon atoms, 1-(alkanoyloxy)ethyl having from 4-9 carbon atoms, 1-methyl-1-(alkanoyloxy)ethyl having from 5-10 carbon atoms, alkoxycarbonyloxymethyl having from 3-6 carbon atoms, 1-(alkoxycarbonyloxy)ethyl having from 4-7 carbon atoms, 1-methyl-1-(alkoxycarbonyloxy) ethyl having from 5-8 carbon atoms, N-(alkoxycarbonyl) aminomethyl having from 3-9 carbon atoms, 1-(N-[alkoxycarbonyl]amino)ethyl having from 4-10 carbon atoms, 3-phthalidyl, 4-crotonolactonyl, gamma-butyrolacton-4-yl, carboxyalkylcarbonyloxymethyl having from 4-12 carbon atoms, or (5-methyl-2-oxo-1,3-dioxolen- 4-yl)methyl. To prepare compounds of formula I or II wherein $R_1$ is a group which forms an ester which is hydrolyzed in vivo, the acid of formula I or II ($R_1$ is hydrogen) is reacted with a base to form the corresponding anion. Suitable cations include sodium, potassium, calcium, tetra-alkylammonium and the like. The anion can be prepared by lyophilizing an aqueous solution of I or II, for example, an aqueous solution containing tetrahydrofuran, and sodium bicarbonate or tetrabutylammonium hydroxide. The anion can also be prepared from an aqueous solution of a tetra-alkylammonium alkali metal cation sulfate, such as tetrabutylammonium sodium sulfate, and the acid of formula I or II at about 20° to about 50° C., preferably about 25° C., followed by extraction and concentration to remove the solvent.

The resulting anion of I or II is reacted with the corresponding chloride or bromide of $R_1$ in a reaction-inert solvent such as acetone or dimethylformamide at about 20° to about 50° C., preferably 25° C.

The compounds of formula II wherein $R_1$ is hydrogen or salt thereof can be synthesized according to Schemes A–C.

As shown in Scheme A, a compound of formula II can be prepared in accordance with the procedure of Yoshida et al, *Chem. Pharm. Bull.*, 29, 2899–2909(1981), from the known dibromo penam of formula IV. The dibromo penam (V) undergoes an exchange reaction with t-butyl magnesium chloride at a temperature of between about −90° and −40° C., preferably about −76° C. in a reaction-inert solvent such as tetrahydrofuran, diethyl ether or toluene, preferably tetrahydrofuran. Other organometallic reagents may also be employed. The resultant reaction mixture is treated in situ with the appropriate aldehyde; e.g., acetaldehyde for the 1-hydroxyethyl derivative. The aldehyde is added at between about −80° and −60° C., preferably about −76° C. for acetaldehyde.

The resulting bromo hydroxy penam V is hydrogenated to remove the 6-bromo substituent. A suitable hydrogenation catalyst is a noble metal catalyst such as palladium. The reaction is carried out in a protic solvent such as 1:1 methanol-water or 1:1 tetrahydrofuran-water, preferably 1:1 methanol-water, at a pressure of about 1 to 4 atms, preferably 4 atm and a temperature of between about 0° and 30° C., preferably about 25° C.

SCHEME A

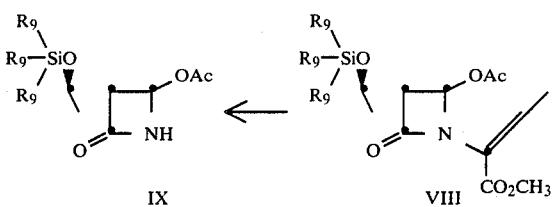

SCHEME B

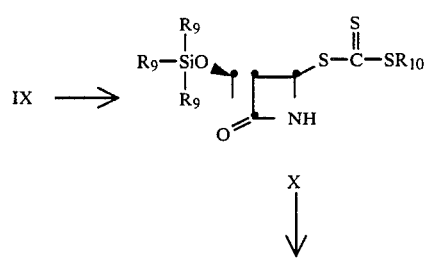

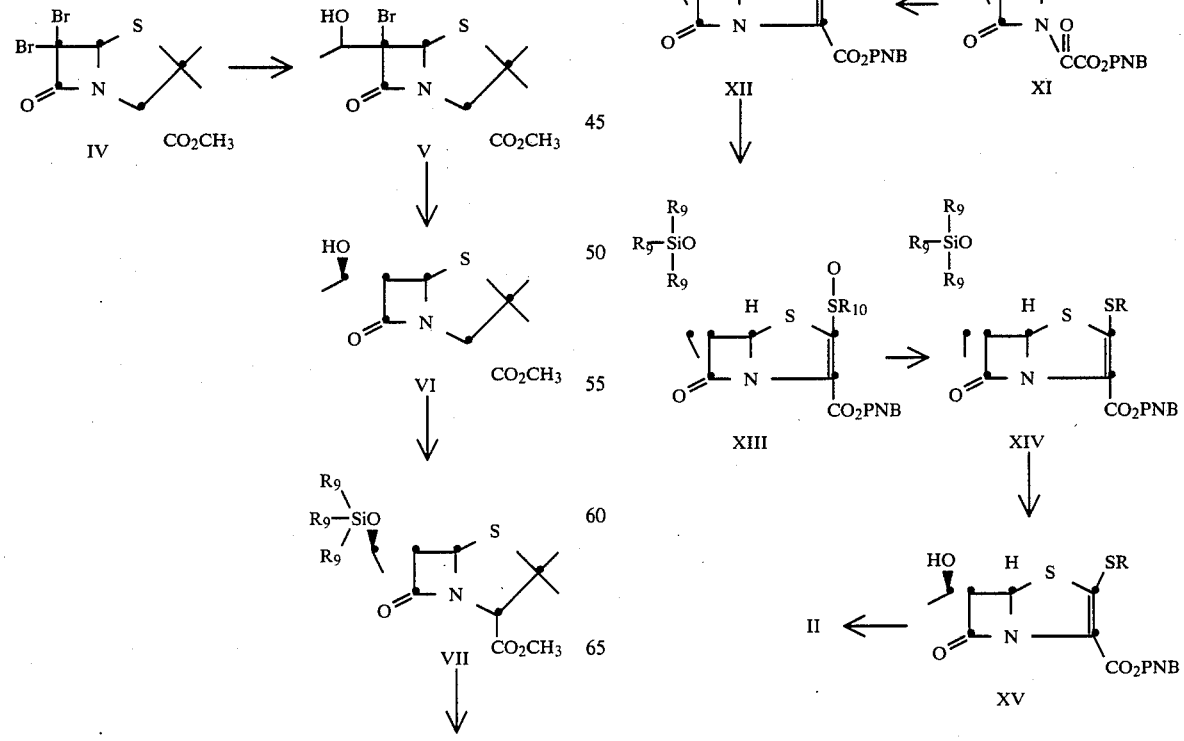

SCHEME C

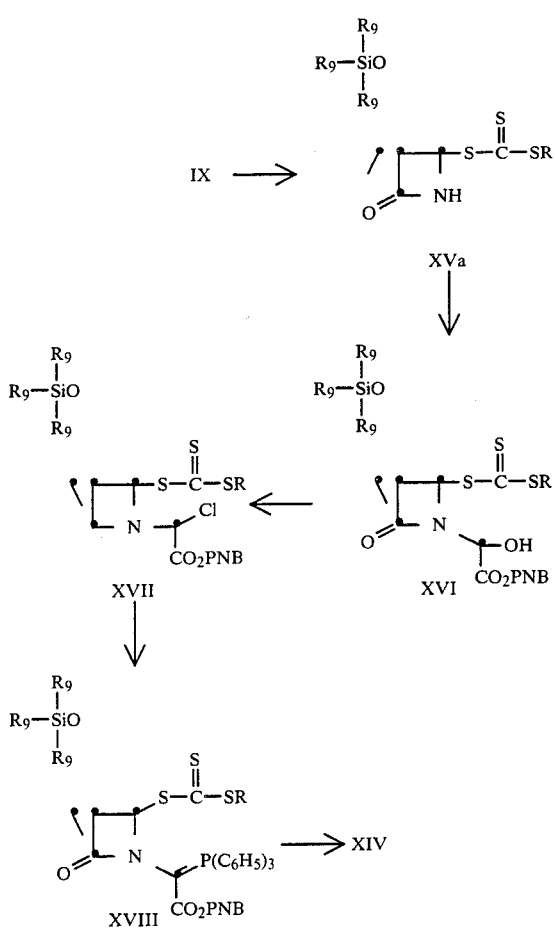

The resulting alcohol of formula VI can be protected with a trialkylhalosilane of formula

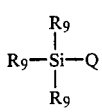

wherein $R_9$ at each occurrance is an alkyl of 1 to 6 carbon atoms and Q is chloro, bromo or iodo. Thus, dimethyl-t-butylchlorosilane in the presence of an amine proton acceptor such as imidazole in a polar, aprotic solvent such as N,N-dimethylformamide at a temperature range of between about 5° and 40° C., preferably about 25° C. forms a trialkylsilyl hydroxyl-protecting group as shown in formula VII.

Treatment of VII with mercuric acetate in acetic acid at a temperature of about 90° C. yields the olefin VIII.

In order to obtain the desired azetidinone IX, the olefin VIII is ozonized in a reaction-inert solvent such as dichloromethane at a temperature of between about −80° and −40°, preferably about −76° C. The reaction product is treated with an alkanol such as methanol to yield the azetidine IX.

As shown in Scheme B, a compound of formula IX is treated with trithiocarbonate salt of the formula $M^+R_{10}$—S—C(S)—S— wherein $R_{10}$ is alkyl having 1-4 carbon atoms, preferably ethyl, and M is a metal such as sodium or potassium to obtain a compound of formula X. This conversion of IX to X is carried out in an organic solvent or water, preferably a mixture of water and dichloromethane at a temperature range of about 0°-35° C., preferably about 25° C.

The compound of formula X is condensed with p-nitrobenzyl chloro-oxalate in the presence of a tertiary alkylamine wherein each alkyl has, for example, 1-4 carbon atoms such ethyl-di-isopropylamine, to obtain the compound of formula XI. This condensation reaction is carried out in a reaction-inert solvent, preferably dichloromethane, at a temperature range of about 5°-25° C., preferably about 10° C.

The resulting compound of formula XI is cyclized using a trialkyl phosphite wherein alkyl has 1-4 carbon atoms such as triethylphosphite in a reaction-inert solvent such as trichloromethane at a temperature range of about 40°-80° C., preferably about 60° C. to obtain the penem of formula XII.

The thiol group of compound XII is oxidized to the corresponding sulfoxide XIII with an oxidizing agent such as m-chloroperbenzoic acid in a reaction inert solvent such as dichloromethane, at a temperature range of about −10° to −30° C., preferably −20° C.

The sulfoxide XIII is substituted with the mercaptide of formula R—S by employing, for example, the sodium or potassium salt which is reacted with the sulfoxide XIII in an polar organic solvent such as ethanol or acetonitrile at a temperature range of about 35° to −50° C., preferably about −35° C.

Starting mercaptans of the formula R—SH or starting thioacetates of the formula R—S—C(O)CH$_3$ are known for many of the values of R and those which are not known can be prepared by analogous methods known in the art. For a review see J. L. Wardell, "Preparation of Thiols," in *The Chemistry of the Thiol Group*, S. Patai, editor, John Wiley & Sons, London, 1974, Chapter 4. See also Volante, *Tetrahedron Letters*, 22, 3119-3122(1981) for the conversion of alcohols to thiols and thiolesters using triphenylphosphine and a dialkyl azodicarboxylate in the presence of the alcohol and an appropriate thiolacid.

Where R groups contain an $S(O)_n$ group and n is 1 or 2, the corresponding sulfide (n is zero) thioacetate R—S—C(O)CH$_3$ can be oxidized with an approximately equimolar amount of m-chloroperbenzoic acid to the sulfoxide (n is one) or with additional m-chloroperbenzoic acid to obtain the sulfone (n is two) without oxidation of the thioacetate sulfur.

The sulfoxide can also be oxidized to the sulfone with potassium permanganate in an aqueous solvent such as aqueous acetone at a buffered pH of about 7 at about 20°-50° C., preferably about 25° C. This method is particularly preferred for an R group containing a hydroxyl group.

Furthermore, cyclic sulfone containing double bonds can be readily isomerized by the procedures of Prochazka et al., *Collection Czech. Chem. Comm.*, 31,3744 (1966).

For compounds of formula XIV the trialkylsilyl group is preferably removed prior to the hydrogenolysis to remove the acid-protecting group (PNB) to obtain a compound of formula XV. the trialkylsilyl group is removed with a tetralkylammonium fluoride in a ethereal solvent such as tetrahydrofuran at a temperature range of about 15° to 40° C., preferably about 25° C.

Conversion of a compound of formula XV to a compound of formula II is accomplished using a conventional hydrogenolysis reaction, and it is carried out in conventional fashion for this type of transformation. Thus, a solution of a compound of the formula XV is stirred or shaken under an atmosphere of hydrogen, or hydrogen mixed with an inert diluent such as nitrogen or argon, in the presence of a catalytic amount of a noble metal hydrogenolysis catalyst, such as a palladium-on-calcium carbonate or a palladium-on-Celite (a diatomaceous earth) catalyst. Convenient solvents for this hydrogenolysis are lower alkanols, such as methanol; ethers, such as tetrahydrofuran and dioxan; low molecular weight esters, such as ethyl acetate and butyl acetate; water; and mixtures of these solvents. However, it is usual to choose conditions under which the starting material is soluble. The hydrogenolysis is usually carried out at room temperature and at a pressure from about 0.5 to about 5 kg/cm$^2$. The catalyst is usually present in an amount from about 10 percent by weight based on the starting material up to an amount equal in weight to the starting material, although larger amounts can be used. The reaction commonly takes about one hour after which the compound of the formula I is recovered simply by filtration followed by removal of the solvent in vacuo. If palladium-on-calcium carbonate is used as the catalyst, the product is often isolated as the calcium salt and if palladium-on-Celite is employed the product is often isolated as the sodium salt.

The compound of formulas I or II can be purified by conventional methods for beta-lactam compounds. For example, the compound of formulas I or II can be purified by column chromatography, gel filtration on Sephadex, or by recrystallization.

An alternate synthetic procedure is shown in Scheme C. The azetidine of formula IX is reacted with a trithiocarbonate of the formula M$^+$R—S—C(S)—S$^-$ wherein M is a metal such a sodium or potassium using the procedure previously described to prepare X.

The resulting trithiocarbonate XVa is treated with (P-nitrobenzyloxycarbonyl)(dihydroxy)methane in an aprotic solvent such as benzene, toluene or dimethylformamide, preferably benzene, at a temperature range of about 25°–110° C., preferably about 80° C. to yield the alcohol of formula XVI.

The corresponding chloride XVII is prepared from the alcohol XVI by treating thionyl chloride in a reaction-inert organic solvent such as dichloromethane in the presence of a hindered amine which serves as an acid acceptor such as 2,6-lutidine at a temperature range of about $-10°$ to 75° C., preferably 0° C.

The chloride XVII is reacted with a triarylphosphine such as triphenylphosphine in a reaction-inert solvent such as tetrahydrofuran in the presence of a tertiary amine such as 2,6-lutidine at a temperature of about 25° C., to obtain the compound of formula XVIII which is cyclized by refluxing in an aromatic solvent such as toluene to yield the penem of formula XIV.

Trithiocarbonate salts of the formula M$^+$R—S—(C=S)—S$^-$ are prepared from the appropriate mercaptan of the formula R—SH or by treatment of a thioacetate of the formula RSC(O)CH$_3$ with an alkaline metal alkoxide followed by carbon disulfide.

By employing the heretofore mentioned procedure of Yoshida et al., the stereochemistry at carbon 6 of the penem as well as the hydroxyethyl group attached to carbon 6 is that shown in formula II. The principal stereo-chemistry for the product of ring closure using Schemes B or C is that wherein the hydrogen at penem ring position 5 is trans to the hydrogen on carbon 6 and in the alpha configuration. Alternatively, the stereochemistry can be described as 5R, 6S; 6-(R)-1-hydroxyethyl.

The compounds of formula I or II are acidic and will form salts with basic agents. Such salts are considered to be within the scope of this invention. These salts can be prepared by standard techniques, such as contacting the acidic and basic components, usually in a stoichiometric ratio, in an aqueous, non-aqueous or partially aqueous medium, as appropriate. They are then recovered by filtration, by precipitation with a non-solvent followed by filtration, by evaporation of the solvent, or in the case of aqueous solutions by lyophilization, as appropriate. Basic agents which are suitably employed in salt formation belong to both the organic and inorganic types, and they include ammonia, organic amines, alkali metal hydroxides, carbonates, bicarbonates, hydrides and alkoxides, as well as alkaline earth metal hydroxides, carbonates, hydrides and alkoxides. Representative examples of such bases are primary amines, such as n-propylamine, n-butylamine, aniline, cyclohexylamine, benzylamine and octylamine; secondary amines, such as diethylamine, morpholine, pyrrolidine and piperidine; tertiary amines, such as triethylamine, N-ethylpiperidine, N-methylmorpholine and 1,5-diazabicyclo[4,3,0]non-5-ene; hydroxides, such as sodium hydroxide, potassium hydroxide, ammonium hydroxide and barium hydroxide; alkoxides, such as sodium ethoxide and potassium ethoxide; hydrides, such as calcium hydride and sodium hydride; carbonates, such as potassium carbonate and sodium carbonate; bicarbonates, such as sodium bicarbonate and potassium bicarbonate; and alkali metal salts of long-chain fatty acids, such as sodium 2-ethylhexanoate.

Preferred salts of the compounds of formula I or II are sodium, potassium and calcium salts.

A pharmaceutically acceptable salt is one in which the resulting compound of formula I or II is non-toxic, useful as a therapeutic agent and has metabolic decomposition products which are non-toxic.

As indicated hereinbefore, the compounds of formula I or II and salts thereof are anti-bacterial agents. The in vitro activity of the compounds of the formula I or II and salts thereof can be demonstrated by measuring their minimum inhibitory concentrations (MIC's) in mcg/ml against a variety of microorganisms. The procedure which is followed is the one recommended by the International Collaborative Study on Antibiotic Sensitivity Testing (Ericcson and Sherris, *Acta. Pathologica et Microbiologia* Scandinav, Supp. 217, Section B: 64–68 [1971]), and employs brain heart infusion (BHI) agar and the inocula replicating device. Overnight growth tubes are diluted 100 fold for use as the standard inoculum (20,000–10,000 cells in approximately 0.002 ml. are placed on the agar surface; 20 ml. of BHI agar/dish). Twelve 2 fold dilutions of the test compound are employed, with initial concentration of the test drug being 200 mcg/ml. Single colonies are disregarded when reading plates after 18 hrs. at 37° C. The susceptibility (MIC) of the test organism is accepted as the lowest concentration of compound capable of producing complete inhibition of growth as judged by the naked eye.

The compounds of formula I or II, and the pharmaceutically-acceptable salts thereof, are suitable for the control of bacterial infections in mammmals, including man. They will find use in the control of infections caused by susceptible bacteria in human subjects, e.g. infections caused by susceptible strains of *Staphylococcus aureus*.

When a compound of formula I or II, or a pharmaceutically-acceptable salt thereof, is used to treat a bacterial infection in a mammalian subject, it can be administered orally or parenterally, i.e. intramuscularly, subcutaneously, intraperitoneally or intravenously. The compound can be administered alone, or it can be combined with a pharmaceutically-acceptable carrier according to standard pharmaceutical practice. The proportional ratio of active ingredient to carrier will naturally depend on the chemical nature, solubility and stability of the active ingredient, as well as the dosage contemplated. However, in a pharmaceutical composition containing an antibacterial agent of the invention, the ratio of the pharmaceutically-acceptable carrier to the penem compound will normally be in the range from 1:10 to 4:1. For the oral mode of administration, an antibacterial penem compound of this invention can be used in the form of tablets, capsules, lozenges, troches, powders, syrups, elixirs, aqueous solutions and suspensions, and the like. In the case of tablets, carriers which can be used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols. When aqueous suspensions are required for oral use, the active ingredient is combined with emulsifying and suspending agents. If desired, certain sweetening and/or flavoring agents can be added. For parenteral administration, sterile solutions of the active ingredient are usually prepared, and the pH of the solutions are suitably adjusted and buffered. For intravenous use, the total concentration of solutes should be controlled to render the preparation isotonic.

As indicated earlier, the compounds of formula I or II are of use as antibacterial agents in human subjects against susceptible organisms. The prescribing physician will ultimately determine the appropriate dose for a given human subject, and this can be expected to vary according to the age, weight, and response of the individual patient, as well as the nature and the severity of the patients' symptoms. The compounds of formula I or II will normally be used orally at dosages in the range from about 10 to about 200 mg. per kilogram of body weight per day, and parenterally at dosages from about 10 to about 400 mg. per kilogram of body weight per day. These figures are illustrative only, however, and in some cases it may be necessary to use dosages outside these limits.

The following Examples and Preparations are provided solely for further illustration. Infra-red (IR) spectra were measured as potassium bromide discs (KBr disc), Nujol mulls (Nujol), or as solutions in chloroform (CHCl$_3$), methylene chloride (CH$_2$Cl$_2$) or dimethyl sulfoxide (DMSO), and diagnostic absorption bands are reported in either microns or wave numbers (cm$^{-1}$). Nuclear magnetic resonance (NMR) spectra were measured at 60 MH$_2$ unless otherwise indicated for solutions in deuterochloroform (CDCl$_3$), perdeutero water (D$_2$O) or perdeuterodimethyl sulfoxide (DMSO-d$_6$), or mixtures thereof, and peak positions are expressed in parts per million (ppm) downfield from tetramethylsilane. The following abbreviations for peak shapes are used: s, singlet; d, doublet; t, triplet; q, quartet; m, multiplet; b, broad; c, complex. The abbreviations "ss" and "sss" denote that a particular proton appeared as two or three singlets respectively, owing to the presence of diastereoisomers. Throughout the Examples and Preparations, the abbreviation "PNB" represents the p-nitrobenzyl group.

EXAMPLE 1

Sodium (5R, 6S)-6-[(R)-1-Hydroxyethyl]-2-(1,1-dioxo-3-thiolanyl)thio-2-penem-3-carboxylate A suspension of 10% palladium on diatomaceous earth (350 mg) in 75 ml. tetrahydrofuran +75 ml. distilled water was adjusted to a pH of 8.3 with 0.02M aqueous sodium bicarbonate. A solution of 350 mg. of p-nitrobenzyl (5R,6S)-6-[(R)-1-hydroxyethyl]-2-(1,1-dioxo-3-thiolanyl)thio-2-penem-3-carboxylate in 50 ml. tetrahydrofuran and 50 ml. water was added and the resulting mixture was hydrogenated at 55 p.s.i. of hydrogen for 75 min.; 350 mg. more of 10% palladium on diatomaceous earth was then added to the reaction mixture and the pH of the suspension was adjusted to 7.0 using 0.02M aqueous sodium bicarbonate. The mixture was hydrogenated at 55 p.s.i. for 75 min., then the catalyst was removed by filtration and the filtrate was concentrated in vacuo to remove tetrahydrofuran. The pH of the resulting aqueous solution was adjusted to 7 and the solution was extracted with two 100 ml. portions of ethyl acetate. The aqueous solution was then lyophilized, yielding 224 mg. of the title compound as an amorphous solid (82.5% yield).

The infrared spectrum of the title compound as a potassium bromide disc showed absorptions at 2.92, 5.65 and 6.3 microns.

EXAMPLE 2

The procedures of Example 1 were employed using the corresponding compound of formula XV to obtain the corresponding sodium salts of formula II for the value of R shown in Table 1 along with the infrared absorptions of the product as a potassium bromide disc unless otherwise indicated.

TABLE 1

| R | IR (microns) | Yield (%) |
| --- | --- | --- |
| 3-thiolanyl | 2.94, 5.66 and 6.3 | 82 |
| cis-1-oxo-3-thiolanyl (from more polar isomer) | 2.92, 5.65 and 6.27 | 78 |
| trans-1-oxo-3-thiolanyl (from less polar isomer) | 2.92, 5.65 and 6.26 | 51 |
| 2-(methylsulfinyl)ethyl | 2.94, 5.65 and 6.3 | 67 |
| 2-(methylsulfonyl)ethyl | 2.94, 5.65 and 6.25 | 59 |
| methylsulfinylmethyl | 2.94, 5.66 and 6.26 | 78 |
| methylsulfonylmethyl | 2.94, 5.62 and 6.28 | 68 |
| 1-oxo-3-thianyl | 2.93, 5.65 and 6.26 | 74 |
| 1,1-dioxo-3-thianyl | 2.94, 5.66 and 6.4 | 67 |
| 3-thietanyl | 2.92, 5.65 and 6.26 | 87 |
| cis-1-oxo-3-thianyl | 5.66 (Nujol) | 98 |
| trans-1-oxo-3- | 5.66 (Nujol) | 92.8 |

EXAMPLE 3

(5R, 6S)-6-[(R)-1-Hydroxyethyl]-2-(cis-1-oxo-4-thianyl)-thio-3-carboxyl-2-penem

Palladium on Celite (10%, 3.00 g) was prehydrogenated at 60 psi for 10 min in a solution of tetrahydrofuran (130 ml) and water (120 ml). The pH was adjusted to 7.5 with 1N hydrochloric acid, then 6.20 g (12.4 mmol) of p-nitrobenzyl (5R, 6S)-6-[(R)-1-hydroxyethyl]-2-(cis-1-oxo-4-thianyl)thio-2-penem-3-carboxylate was added and the slurry was hydrogenated for 0.5 hour. For two times catalyst (3.00 g) was added, the pH was adjusted to 7.0, and the reaction mixture hydrogenated for 0.75 hour. A final charge of catalyst was added, the pH was adjusted to 7.3, and the reaction mixture hydrogenated for 1.5 hours. The reaction mixture was filtered through a pad of Celite and washed with additional tetrahydrofuran-water (1:1). The tetrahydrofuran was removed in vacuo. The insolubles were removed by filtration through Celite, and the pH of the filtrate was adjusted to 7.0. The aqueous portion of the filtrate was washed two times with ethyl acetate, concentrated to remove residual ethyl acetate, cooled with an ice bath and the pH adjusted to 2.3 with 6N hydrochloric acid. After 30 min, a precipitated solid was collected by filtration. Drying the precipitate in vacuo to a constant weight afforded 3.64 g (81% yield) of the title compound as a mustard-yellow solid, mp 149°–151° C., $[\alpha]_9$(DMSO): +153°.

The nmr spectrum (250 MHz) of the title compound as a perdeuterodimethylsulfoxide solution showed peaks at 1.16 (d, J=6.2 Hz, 3H), 1.95–2.3 (m, 4H), 2.7–3.0 (m, 4H), 3.3–3.4 (m, 1H), 3.79 (dd, J=6.1, 1.4 Hz, 1H), 3.98 (m, 1H), 5.20 (bs, 1H), and 5.71 (d, J=1.4 Hz, 1H) ppm. The infrared spectrum of the title compound as a potassium bromide disc showed absorptions at 2950 (b), 2923, 1782, 1678, 1508, 1400, 1294, 1216, 1197, 1131, 949, and 935 cm$^{-1}$. The ultraviolet spectrum of a dimethylsulfoxide solution of the title compound had the following absorption maxima, with the extinction coefficient in parentheses: 267 (4840) and 337 (6720) nanometers.

EXAMPLE 4

Sodium (5R, 6S)-6-[(R)-1-Hydroxyethyl]-2-(cis-1-oxo-4-thianyl)thio-2-penem-3-carboxylate The title compound of Example 3 (5.09 g, 14.0 mmol) was suspended in 75 ml of water and cooled with an ice bath. The pH of the reaction mixture was adjusted to 7.00 by the addition of 1.00N aqueous sodium hydroxide (13.0 ml, 93% of theoretical). The homogeneous solution was lyophilized overnight, affording 5.00 g (93% yield) of the title compound as a beige solid, $[\alpha]_D$(H$_2$O): +111.4°.

The nmr spectrum (250 MHz) of a D$_2$O solution of the title compound showed peaks at 1.29 (d, J=6.4 Hz, 3H), 2.1–2.4 (m, 4H), 2.8–3.0 (m, 2H), 3.1–3.25 (m, 2H), 3.42 (m, 1H), 3.91 (dd, J=5.9, 1.0 Hz), 1H), 4.24 (qd, J=6.4, 5.9, 1H), and 5.67 (d, J=1.0 Hz, 1H) ppm. The infrared spectrum of the title compound as a potassium bromide disc showed absorptions at 3403, 2964, 2917, 1765, 1589, 1514, 1372, 1290, 1126, 1041, 1012, 988, and 936 cm$^{-1}$. The ultraviolet spectrum of an aqueous solution of the title compound had the following absorptions maxima, with the extinction coefficient in parentheses: 259 (5530) and 322 (7260) nanometers.

EXAMPLE 5

Calcium (5R 6S)-6-[(R)-1-Hydroxyethyl]-2-(4-thianyl)-thio-2-penem-3-carboxylate

The hydrogenation procedure of Example 1 was employed using 5 percent palladium on calcium carbonate as the catalyst in 1:1 tetrahydrofuran-water and p-nitrobenzyl (5R, 6S)-6-[hydroxyethyl]-2-(4-thianyl)thio-2-penem-3-carboxylate as the starting material to obtain the title compound in 100% yield.

The NMR spectrum (250 MHz) of the title compound as a perdeuterowater solution showed peaks at 1.29 (3H, d, J=6.4 Hz), 1.7–1.9 (2H, m), 2.3–2.5 (2H, m), 2.7–2.8 (4H, m), 3.30 (1H, tt), 3.90 (1H, dd, J=6.0, 1.3 Hz), 4.24 (1H, m), and 5.65 (1H, d, J=1.3 Hz) ppm.

The infrared spectrum of the title compound as a potassium bromide disc showed absorptions at 3409, 1770, 1583 and 1385 cm$^{-1}$.

EXAMPLE 6

The procedure of Example 5 were employed using as the starting material p-nitrobenzyl (5R, 6S)-6-[(R)-1-hydroxyethyl]-2-(1,1-dioxo-4-thianyl)thio-2-penem-3-carboxylate to obtain calcium (5R, 6S)-6-[(R)-1-hydroxyethyl]-2-(1,1-dioxo-4-thianyl)thio-2-penem-3-carboxylate in 93% yield.

The NMR spectrum (250 MHz) of the product as a perdeuterowater solution showed peaks at 1.29 (3H, d), 2.15–2.4 (2H, m), 2.4–2.65 (2H, m), 3.2–3.45 (4H, m), 3.61 (1H, m), 3.95 (1H, dd), 4.26 (1H, m), and 5.68 (1H, d) ppm.

The infrared spectrum of the product as a potassium bromide disc showed absorptions at 3421, 1767, 1588, 1382, 1286 and 1112 cm$^{-1}$.

Similarly, the procedures of Example 5 were employed using as the starting material p-nitrobenzyl (5R, 6S)-6-[(R)-1-hydroxyethyl]-2-(trans-1-oxo-4-thianyl)thio-2-penem-3-carboxylate to obtain calcium (5R 6S)-6-[(R)-1-hydroxyethyl]-2-(trans-1-oxo-4-thianyl)thio-2-penem-3-carboxylate in 81% yield. The infrared spectrum of a potassium bromide disc of the product had absorption at 1769, 1592, 1511, 1383, 1294, 1131, and 1021 cm$^{-1}$.

The NMR spectrum (250 MHz) of a perdeuterowater solution of the product had peaks at 1.29 (3H, d, J=6.3 Hz); 1.85–2.1 (2H, m); 2.45–2.65 (2H, m); 2.85–3.0 (2H, m); 3.15–3.4 (2H, m); 3.63 (1H, m); 3.93 (1H, dd, J=6,1 Hz); 4.26 (1H, qd, J=6.3, 6 Hz; and 5.68 (1H, d, J=1 Hz) ppm.

EXAMPLE 7

Sodium (5R, 6S)-6-[(R)-1-Hydroxyethyl]-2-[(cis)-1-oxo-3-thiolanyl]thio-2-penem-3-carboxylate To a solution of 6.0 g. p-nitrobenzyl (5R, 6S)-6-[(1R)-1-hydroxyethyl-2-[(cis)-1-oxo-3-thiolanyl]thio-2-penem-3-carboxylate in 100 ml. tetrahydrofuran and 25 ml. water was added a suspension of 3.0 g. of 10% palladium on diatomaceous earth in 100 ml. water which had been adjusted to pH 7.4, followed by 25 ml. of tetrahydrofuran. The resulting mixture was hydrogenated at 60 p.s.i. of hydrogen for 10 min. another 3.0 g. of catalyst was added and the pH of the mixture was adjusted to 7.3 with dilute aqueous sodium bicarbonate solution. The mixture was hydrogenated at 60 p.s.i. for 25 min., then 4.0 g. more catalyst was added and the pH of the suspension was adjusted to 7.4 with dilute aqueous sodium bicarbonate solution. The mixture was hydrogenated at 60 p.s.i. for 45 min., then the pH was adjusted to 6.9 with aqueous sodium bicarbonate solution and the catalyst was removed by filtration. The filtrate was concentrated in vacuo to remove tetrahydrofuran and the aqueous solution was washed with 200 ml. diethyl ether, 200 ml. ethyl acetate and 200 ml. diethyl ether. The solution was filtered and the pH of the filtrate was adjusted to 7.2. Lyophilization of this solution yielded 4.3 g. (93% yield) of the title product as an amorphous solid.

The NMR spectrum (250 MHz) of a solution of the title compound in perdeuterowater had peaks at 1.32 (d, 3H); 2.53 (c, 1H); 2.74–3.12 (c, 3H); 3.26 (c, 1H); 3.83–4.09 (c, 3H); 4.27 (m, 1H); and 5.74 (2d, 1H) ppm.

The infrared spectrum of a potassium bromide disc of the title compound had absorptions at 2.93, 5.66 and 6.3 microns.

EXAMPLE 8

Sodium (5R, 6S)-6-[(R)-1-Hydroxyethyl-2-[(trans)-1-oxo-3-thiolanyl]thio-2-penem-3-carboxylate The procedure of Example 7 were employed with p-nitrobenzyl (5R, 6S)-6-[(R)-1-hydroxyethyl-2-[(trans)-1-oxo-3-thiolanyl]thio-2-penem-3-carboxylate as the starting material to obtain the title compound in 80% yield.

The NMR spectrum (250 MHz) of a solution of the title compound in perdeuterowater had peaks at 1.32 (d, 3H); 2.27 (m, 1H); 2.78–3.18 (c, 2H); 3.47 (c, 2H); 3.66 (m, 1H); 3.97 (m, 1H); 4.22–4.43 (c, 2H); and 5.74 (d, 1H) ppm.

The infrared spectrum of a potassium bromide disc of the title compound had absorptions at 2.92, 5.65 and 6.26 microns.

EXAMPLE 9

Sodium (5R, 6S)-6-[(R)-1-Hydroxyethyl]-2-(2-oxo-1,3-dithiolan-4-ylmethyl)thio-2-penem-3-carboxylate A suspension of 110 mg of 10% palladium on Celite diatomaceous earth catalyst in 10 ml. water was adjusted to pH 7. Then a solution of 107 mg p-nitrobenzyl (5R, 6S)-6-[(R)-1-hydroxyethyl]-2-(2-oxo-1,3-dithiolan-4-ylmethyl)thio-2-penem-3-carboxylate in 10 ml tetrahydrofuran was added and the resulting reaction mixture was hydrogenated for 1 hour at room temperature and 50 psi. Two additional charges of catalyst were added at 1 hour intervals. The catalyst was filtered off and the filtrate was evaporated to remove tetrahydrofuran. The aqueous solution remaining was washed with ethyl acetate and with diethyl ether and was then filtered. The filtrate was freeze dried to give the title compound (60 mg) as a pale yellow powder.

IR(KBr): 1600, 1640, and 1778 cm$^{-1}$.

NMR (D$_2$O;25 OMHZ): 1.29(3H,d,J=6); 3.25–3.63(2H,m); 3.72–4.12(2H,m); 4.24(1H,m); and 5.66 (1H,s) ppm. (Some peaks obscured by solvent).

EXAMPLE 10

Preparation and Separation of Diastereomers of Sodium (5R, 6S)-6-([(R)-1-Hydroxyethyl]-2-(1,1-dioxo-3-thiolanyl)thio-2-penem-3-carboxylate The procedure of Preparation F were repeated to obtain p-nitrobenzyl (5R, 6S)-6-[(R)-1-t-butyldimethylsilyloxyethyl]-2-(1,1-dioxo-3-thiolanyl)thio-2-penem-3-carboxylate in 50.8% yield. The two diastereomers of the product were separated by column chromatography on silica gel eluting with 1:1 ethyl acetate/hexane.

The less polar diastereomer was obtained in 46.5% yield and had a melting point of 160.5°–162° C.; its infrared spectrum as a potassium bromide disc had absorptions at 5.62, 5.97, 6.56 and 6.74 microns; and its NMR spectrum (250 MHz) as a deuterochloroform solution had peaks at 0.03 (S, 3H); 0.07 (S, 3H); 0.81 (S, 9H); 1.25 (d, 3H); 2.28 (m, 1H); 2.76 (m, 1H); 3.12 (c, 2H); 3.34 (m, 1H); 3.58 (m, 1H); 3.79 (m, 1H); 3.98 (m, 1H); 4.28 (m, 1H); 5.32 (q, 2H); 5.71 (d, 1H); 7.6 (d, 2H); and 8.21 (d, 2H) ppm.

The more polar isomer was obtained in 40.3 percent yield and had a melting point of 181.5°–182° C., its infrared spectrum as a potassium bromide disc had absorptions at 5.62, 5.9, 6.6 and 6.67 microns; and its NMR spectrum (250 MHz) as a deuterochloroform solution had peaks at 0.02 (S, 3H); 0.05 (S, 3H); 0.82 (S, 9H); 1.24 (d, 3H), 2.24 (m, 1H); 2.71 (m, 1H); 3.14 (c, 2H); 3.33 (m, 1H); 3.71 (m, 1H); 3.78 (m, 1H); 3.97 (m, 1H); 4.28 (m, 1H); 5.32 (q, 2H); 5.72 (d, 1H); 7.61 (d, 2H); and 8.21 (d, 2H) ppm.

p-nitrobenzyl (5R, 6S)-6-[(R)-1-hydroxyethyl]-2-(1,1-dioxo-3-thiolanyl)thio-2-penem-3-carboxylate diastereomer from the less polar silyl ether diastereomer The less polar silyl ether was reacted according to Preparation A to obtain the corresponding 1-hydroxyethyl compound, m.p. 172°–173° C., 80% yield. The infrared spectrum of a potassium bromide disc of the product had absorptions at 5.63, 5.94, 6.6 and 6.68 microns. The NMR spectrum (250 MHz) of a deuterochloroform/perdeuterodimethyl sulfoxide solution of the product had peak at 1.32 (d, 3H); 2.3 (m, 1H); 2.76 (m, 1H); 3.15 (c, 2H); 3.34 (m, 1H); 3.59 (m, 1H); 3.78 (m, 1H); 4.09 (c, 2H); 5.1 (d, 1H); 5.36 (q, 2H); 5.77 (d, 1H); 7.65 (d, 2H); and 8.22 (d, 2H) ppm.

p-nitrobenzyl (5R, 6S)-6-[(R)-1-hydroxyethyl]-2-(1,1-dioxo-3-thiolanyl)thio-2-penem-3-carboxylate diastereomer from the more polar silyl ether diastereomer The more polar silyl ether was reacted according to Preparation A to obtain the corresponding 1-hydroxyethyl compound, m.p. 175°–176° C., 76% yield. The infrared spectrum of a potassium bromide disc of the product had absorptions at 2.86, 5.6, 5.93, 6.59 and 6.68 ppm. The NMR spectrum (250 MHz) of a deuterochloroform-perdeuterodimethyl sulfoxide solution of the product had peaks at 1.34 (d, 3H); 2.25 (m, 1H); 2.69 (m, 1H); 3.16 (c, 2H); 3.35 (m, 1H); 3.71 (m, 1H); 3.78 (m, 1H); 4.03 (m, 1H); 4.16 (m, 1H); 4.88 (d, 1H); 5.35 (q, 2H); 5.78 (d, 1H); 7.64 (d, 2H); and 8.23 (d, 2H) ppm.

title compound diastereomer derived from the less polar silyl ether diastereomer The p-nitrobenzyl 1-hydroxyethyl diastereomer obtained from the less polar silyl ether diastereomer was reacted according to Example 1 to obtain a diastereomer of the title compound in 96% yield. The infrared spectrum of the product as a potassium bromide disc had absorptions at 2.93, 5.65 and 6.29 microns. The NMR spectrum (250 MHz) of a perdeuterowater solution of the product had peaks at 1.39 (d, 3H); 2.45 (m, 1H); 2.86 (m, 1H); 3.38 (c, 2H); 3.56 (m, 1H); 3.82 (m, 1H); 4.06 (m, 1H); 4.25 (m, 1H); 4.36 (m, 1H); and 5.82 (d, 1H) ppm.

title compound diastereomer derived from the more polar silyl ether diastereomer The p-nitrobenzyl 1-hydroxyethyl diastereomer obtained from the more polar silyl ether diastereomer was reacted according to Example 1 to obtain a diastereomer of the title compound in 95.5% yield. The infrared spectrum of the product as a potassium bromide disc had absorptions at 2.94, 5.66 and 6.27 microns. The NMR spectrums (250 MHz) of a perdeuterowater solution of the title comound had peaks at 1.35 (d, 3H); 2.3 (m, 1H); 2.76 (m, 1H); 3.44 (c, 3H); 3.88 (m, 1H); 3.99 (m, 1H); 4.19 (m, 1H); 4.32 (m, 1H); and 5.76 (d, 1H) ppm.

EXAMPLE 11

Preparation, Separation and Transformations of Diastereomers of p-Nitrobenzyl (5R, 6S)-6-[(R)-1-t-Butyldimethylsiloxyethyl]-2-[(cis)-3-hydroxy-4-thiolanyl]thio-2-penem-3-carboxylate To a solution of 0.272 g (0.002 mole) of cis-4-hydroxythiolanyl-3-thiol in 10 ml. anhydrous ethanol cooled to $-30°$ C. under nitrogen was added 2 ml. of a 1M solution (0.002 mole) of sodium ethoxide in ethanol. After stirring for 30 min. at $-30°$ C., the solution was cooled to $-60°$ C. and a solution of 1.08 g (0.002 mol) p-nitrobenzyl (5R, 6S)-6-[(R)-1-t-butyldimethylsiloxyethyl]-2-ethylsulfinyl-2-penem-3-carboxylate in 30 ml. tetrahydrofuran which had been cooled to $-60°$ C. was added. After 15 min. at $-60°$ C. a solution of 0.5 ml acetic acid in 3 ml. tetrahydrofuran was added and the solution was allowed to warm to 25° C. and concentrated in vacuo. The residue was dissolved in ethyl acetate (100 ml) and the resulting solution was washed with 20 ml. water, 20 ml. saturated aqueous sodium bicarbonate solution, 20 ml. water, 20 ml. saturated aqueous sodium chloride solution, dried over anhydrous sodium sulfate and concentrated to dryness. The residue was chromatographed twice on silica gel (250 g and 400 g respectively), eluting with 60:40 hexane-ethyl acetate to yield 0.4 g of the less polar diastereomer (Diastereomer A), 0.56 g. of the more polar diastereomer (Diastereomer B) and 0.12 g of a mixture of diastereomers (90.7% total yield).

Diastereomer A

IR (KBr dis): 2.86, 5.64, 6.0 6.55 and 6.75 microns.
NMR (CDCl$_3$, 250 MHz): 0.04 (s, 3H); 0.07 (s, 3H); 0.83 (s, 9H); 1.25 (d, 3H); 2.47 (d, 1H); 3.0 (m, 2H); 3.15 (m, 2H); 3.68 (m, 1H); 3.78 (dd, 1H); 4.28 (m, 1H); 4.65 (m, 1H); 5.34 (q, 2H); 5.67 (d, 1H); 7.64 (d, 2H); and 8.22 (d, 2H) ppm.

Diastereomer B

IR (KBr disc): 2.86, 5.59, 5.94, 6.59 and 6.68 microns.
NMR (CDCl$_3$, 250 MHz): 0.04 (s, 3H); 0.07 (s, 3H); 0.83 (s, 9H); 1.25 (d, 3H); 2.35 (d, 1H); 3.02 (m, 2H); 3.2 (m, 2H); 3.67 (m, 1H); 3.75 (dd, 1H); 4.28 (m, 1H); 4.59 (m, 1H); 5.34 (q, 2H); 5.67 (d, 1H); 7.62 (d, 2H); and 8.21 (d, 2H); ppm.

p-nitrobenzyl (5R, 6S)-6-[(R)-1-hydroxyethyl]-2-[(cis-3-hydroxy-4-thiolanyl]thio-2-penem-3-carboxylate derived from Diastereomer A The procedures of Preparation A were employed with Diastereomer A as the starting material to obtain the title diol compound in 63.4% yield, melting point 187°–189° C. (with decomposition).

IR (KBr disc); 2.83, 2.90, 5.61, 5.96, 6.58 and 6.71 microns.
NMR (DMSO-d$_6$, 250 MHz): 1.28 (d, 3H); 2.74 (dd, 1H); 2.96 (dd, 1H); 3.13 (m, 2H); 3.63 (m, 1H); 3.89 (dd, 1H); 4.02 (m, 1H); 4.54 (m, 1H); 5.24 (d, 1H); 5.36 (q, 2H); 5.74 (d, 1H); 5.81 (d, 1H); 7.69 (d, 2H); and 8.24 (d, 2H) ppm.

p-nitrobenzyl (5R, 6S)-6-[(R)-1-hydroxyethyl]-b 2-[(cis)-3-hydroxy-4-thiolanyl]thio-2-penem-3-carboxylate derived from Diastereomer B The procedures of Preparation A were employed with Diastereomer A as the starting material to obtain the corresponding diol compound in 77.3% yield, melting point 206°–207° C. (with decomposition).

IR (KBr disc) 2.86, 2.91, 5.63, 5.98, 6.57 and 6.77 microns.
NMR (DMSO-d$_6$, 250 MHz); 1.17 (d, 3H); 2.73 (dd, 1H); 2.93 (dd, 1H); 3.1 (dd, 1H); 3.29 (m, 1H); 3.64 (m, 1H); 3.86 (dd, 1H); 4.02 (m, 1H); 4.5 (m, 1H); 5.24 (d, 1H); 5.37 (q, 2H); 5.77 (d, 1H); 5.79 (d, 1H); 7.69 (d, 2H); and 8.24 (d, 2H) ppm.

sodium (5R, 6S)-6-[(R)-1-hydroxyethyl]-2-[(cis)-3-hydroxy-4-thiolanyl]thio-2-penem-3-carboxylate derived from Diastereomer A The procedures of Example 1 were employed with p-nitrobenzyl (5R, 6S)-6-[(R)-1-hydroxyethyl]-2-[(cis3-hydroxy-4-thiolanyl]thio-2-penem-3-carboxylate derived from Diastereomer A as the starting material to obtain the corresponding sodium salt of formula II in 90% yield.

IR (KBr disc): 2.93, 5.65 and 6.31 microns.
NMR (D$_2$O, 250 MHz): 1.32 (d, 3H); 2.92 (m, 2H); 3.22 (m, 2H); 3.78 (m, 1H); 3.95 (dd, 1H); 4.27 (m, 1H); 4.7 (m, 1H); and 5.7 (d, 1H) ppm.

sodium (5R, 6S)-6-[(R)-hydroxyethyl]-2-[(cis-3-hydroxy-4-thiolanyl]thio-2-penem-3-carboxylate derived from Diastereomer B The procedures of Example 1 were employed with p-nitrobenzyl (5R, 6S)-6-[(R)-1-hydroxyethyl]-2-[(cis)-3-hydroxy-4-thiolanyl]thio-2-penem-3-carboxylate derived from Diastereomer B as the starting material to obtain the corresponding sodium salt of a compound of formula II in yield.

IR (KBr): 2.93, 5.65, and 6.29 microns.

NMR (D₂O, 250 MHz): 1.32 (d, 3H); 2.94 (m, 2H); 3.2 (dd, 1H): 3.34 (dd, 1H); 3.78 (m, 1H); 3.94 (dd, 1H); 4.27 (m, 1H); 4.66 (m, 1H); and 5.71 (d, 1H) ppm.

preparation and separation of isomers of p-nitrobenzyl (5R, 6S)-6-[(R)-1-t-butyldimethylsilyloxymethyl]-2-(1-oxo-3-hydroxy-4-thiolanyl)thio-2-penem-3-carboxylate To a solution of 0.46 g. (0.77 mole) Diastereomer B in 40 ml. methylene chloride cooled to −25° C. under nitrogen was added dropwise over 15 min. a solution of 0.142 g. (0.77 mmole) m-chloroperbenzoic acid (85% activity) in 20 ml. methylene chloride. The solution was stirred at −25° C. for 10 min. after completion of the addition, then 40 ml. methylene chloride and 20 ml. water were added, any excess peracid was destroyed with sodium bisulfite and the pH of the mixture was adjusted to 7.5 with saturated aqueous sodium bicarbonate solution. The methylene chloride layer was separated and washed with 30 ml. water and 30 ml. saturated aqueous sodium chloride solution, dried over anhydrous sodium sulfate and concentrated in vacuo. The residue was chromatographed on silica gel (250 g.), eluting with 92.5:7.5 ethyl acetate-methanol to yield 0.136 g. (28.8% yield) a less polar sulfoxide (Isomer E) and 0.210 g. (44.5%) of a more polar sulfoxide (Isomer F).

In a similar manner oxidation of Diastereomer A with m-chloroperbenzoic acid yielded 0.112 g (38%) of a less polar sulfoxide (Isomer C) and 0.18 g (61.2%) of a more polar sulfoxide (Isomer D).

For Isomers C–F, the infrared spectra were measured as potassium bromide discs and the NMR spectra were measured as perdeuterodimethylsulfoxide solution at 250 MHz. The results are in Table 2.

TABLE 2

| Isomer | IR (microns) | NMR (ppm) |
|---|---|---|
| C | 3.06, 5.56, 5.85 and 6.61 | 0.01 (s, 3H); 0.04 (s, 3H); 0.78 (s, 9H); 1.22 (d, 3H); 2.9 (dd, 1H); 3.15 (m, 2H); 3.59 (dd, 1H); 4.05 (m, 1H); 4.25 (m, 1H); 4.34 (m, 1H); 4.79 (m, 1H); 5.34 (q, 2H); 5.75 (d, 1H); 6.03 (d, 1H); 7.7 (d, 2H); and 8.23 (d, 2H); |
| D | 3.0, 5.59, 5.96 6.57 and 6.77 | 0.01 (s, 3H); 0.04 (s, 3H); 0.78 (s, 9H); 1.21 (d, 3H); 2.88 (m, 2H); 3.27 (dd, 1H); 3.77 (m, 1H); 4.03 (c, 2H); 4.24 (m, 1H); 4.63 (m, 1H); 5.35 (q, 2H); 5.73 (d, 1H); 5.96 (d, 1H); 7.7 (d, 2H); 8.23 (d, 2H); |
| E | 2.98, 5.58, 5.92 6.58, and 6.67 | 0.01 (s, 3H); 0.04 (s, 3H); 0.78 (s, 9H); 1.2 (d, 3H); 2.9 (dd, 1H); 3.08 (dd, 1H); 3.35 (m, 1H); 3.56 (dd, 1H); 4.02 (m, 1H); 4.27 (m, 2H); 4.75 (m, 1H); 5.32 (q, 2H); 5.78 (d, 1H): 5.9 (d, 1H); 7.68 (d, 2H); and 8.22 (d, 2H). |
| F | 2.96, 5.61, 5.98 6.58 and 6.69 | 0.01 (s, 3H); 0.04 (s, 3H); 0.77 (s, 9H); 1.2 (d, 3H); 2.85 (m, 2H); 3.29 (dd, 1H); 3.77 (m, 1H); 4.0 (d, 1H); 4.13 (dd, 1H); 4.23 (m, 1H); 4.56 (m, 1H); 5.34 (q, 2H); 5.76 (d, 1H); 5.98 (d, 1H); 7.69 (d, 2H); and 8.22 (d, 2H). | preparation from Isomer C-F of corresponding p-nitrobenzyl (5R, 6S)-6[(R)-1-hydroxyethyl]-2-(1-oxo-3-hydroxy-4-thiolanyl)thio-2-penem-3-carboxylate isomers The procedures of Preparation A was employed using Isomers C–F as starting materials to obtain the corresponding compounds of formula XV. As shown in Table 3, the infrared spectra were as potassium bromide discs, the NMR spectra were as perdeuterodimethyl sulfoxide solutions and the melting points were all with decomposition.

TABLE 3

| Starting Isomer | IR (microns) | NMR (ppm) | M.P. (°C.) | Yield (%) |
|---|---|---|---|---|
| C | 2.92, 3.12, 5.60, 5.91 and 6.59 | 1.2 (d, 3H); (dd, 1H); 3.15 (m, 2H); 3.58 (dd, 1H); 3.94 (m, 1H); 4.04 (m, 1H); 4.34 (m, 1H); 4.79 (m, 1H); 5.24 (d, 1H); 5.38 (q, 2H); 5.78 (d, 1H); 6.03 (d, 1H); 7.7 (d, 2H); and 8.25 (d, 2H). | 203–5 | 69.9 |
| D | 2.95, 5.59, 5.93 and 6.59 | 1.18 (d, 3H); 2.88 (m, 2H); 3.27 (dd, 1H); 3.78 (m, 1H); 3.9 (dd, 1H); 4.02 (c, 2H); 4.63 (m, 1H); 5.25 (d, 1H); 5.38 (q, 2H); 5.75 (d, 1H); 5.98 (d, 1H); 7.71 (d, 2H); and 8.24 (d, 2H). | 118–20 | 78.5 |
| E | 2.90, 3.11, 5.63, 5.93, 6.58 and 6.68 | 1.17 (d, 3H); 29 (dd, 1H); 3.08 (dd, 1H); 3.35 (dd, 1H); 3.56 (dd, 1H); 3.88 (dd, 1H); 4.02 (m, 1H); 4.28 (m, 1H); 4.74 (m, 1H); 5.23 (d, 1H); 5.37 (q, 2H); 5.79 (d, 1H); 5.98 (d, 1H); 7.68 (d, 2H); and 8.24 (d, 2H). | 216–19 | 42.9 |
| F | 2.86, 3.12, 5.62, 5.95, 6.58 and 6.70 | 1.18 (d, 3H); 2.85 (m, 2H); 3.28 (dd, 1H); 3.76 (m, 1H) 3.86 (dd, 1H). 4.06 (c, 2H); 4.55 (m, 1H); 5.25 (d, 1H); 5.38 (q, 2H); 5.77 (d, 1H); 5.97 (d, 1H); 7.7 (d, 2H); and 8.24 (d, 2H). | 128–30 | 69.2 | preparation of sodium (5R, 6S)-6-[(R)-1-hydroxyethyl]-2-(1-oxo-3-hydroxy-4-thiolanyl]thio-2-penem-3-carboxylate isomers dereved from Isomers C–F The procesdures of Example 1 was empolyed using as starting materials the compounds of formula XV obtained from the corresponding Isomer C–F to obtain coresponding sodium salts of the compounds of formula II. In Table 4, the infrared spectra as potassium bromide discs and the NMR spectra at 250 MHz as perdeuterowater solutions for the product compounds of formula II derived from Isomers C–F, respectively as shown.

TABLE 4

| Isomer | IR (microns) | NMR (ppm) | Yield (%) |
|---|---|---|---|
| C | 2.92, 5.66 and 6.27 | 1.31 (d, 3H); 3.11 (dd, 1H); 3.26 (dd, 1H); 3.44 (dd, 1H); 3.84 (dd, 1H); 3.96 (dd, 1H); 4.25 (m, 1H); 4.4 (m, 1H); 4.93 (m, 1H); and 5.71 (d, 1H). | 46.3 |
| D | 2.96, 5.67 and 6.28 | 1.3 (d, 3H); 3.0 (dd, 1H); 3.17 (dd, 1H); 3.32 (dd, 1H): | 63.3 |

TABLE 4-continued

| Isomer | IR (microns) | NMR (ppm) | Yield (%) |
|---|---|---|---|
| | | 3.83 (m, 1H); 3.94 (dd, 1H); 4.24 (m, 2H); 4.7 (m, 1H); and 5.68 (d, 1H). | |
| E | 2.93, 5.67 and 6.3 | 1.31 (d, 3H); 3.14 (dd, 1H) 3.28 (dd, 1H); 3.55 (dd, 1H); 3.8 (dd, 1H); 3.96 (dd, 1H); 4.26 (m, 1H); 4.38 (m, 1H); 4.92 (m, 1H); and 5.74 (d, 1H). | 60 |
| F | 2.93, 5.65 and 6.30 | 1.3 (d, 3H); 3.03 (dd, 1H); 3.16 (dd, 1H); 3.34 (dd, 1H); 3.83 (m, 1H); 3.93 (dd, 1H); 4.28 (m, 2H); 4.68 (m, 1H); and 5.71 (d, 1H). | 47.1 |

Preparation of diastereomers of p-nitrobenzyl (5R, 6S)-6-[(R)-1-t-butyldimethylsilyloxy]-2-(1,1-dioxo-cis-3-hydroxy-4-thiolanyl]thio-2-penem-3-carboxylate To a solution of 0.12 g. (0.195 mmole) Isomer F in 25 ml. acetone, 5 ml. water and 5 ml. pH 7 buffer ($K_2HPO_4$/NaOH 0.05M) was added dropwise over 20 min. a solution of 15.4 mg (0.097 mmole) potassium permanganate in 30 ml. water. Thin layer chromatography analysis indicated the presence of starting material in the reaction mixture so 4 mg. more of potassium permanganate dissolved in 1 ml. water was added. The acetone was then removed in vacuo and the aqueous layer was extracted with three 50 ml. portions of ethylacetate. The combined ethylacetate extracts were washed with two 30 ml portions of water and 30 ml. saturated aqueous sodium chloride solution, dried over anhydrous sodium sulfate and concentrated in vacuo. The residue was chromatographed on silica gel (50 g.), eluting with 70:30 ethyl acetate-hexane to yield 0.1 g (81% yield) of the corresponding sulfone (Diastereomer H) as a light yellow foam. In a similar manner, 95 mg. of Isomer D was oxidized with potassium permanganate to yield 76 mg. (78%) of the corresponding sulfone (Diastereomer G).

Diastereomer G

IR (KBr disc): 2.88, 5.59, 5.98, 6.57 and 6.75 microns.
NMR ($CDCl_3$ 250 MHz): 0.04 (s, 3H); 0.07 (s, 3H); 0.83 (s, 9H); 1.26 (d, 3H); 3.22 (b, 1H); 3.44 (c, 4H); 3.84 (dd, 1H); 4.04 (m, 1H); 4.28 (m, 1H); 4.73 (m, 1H); 5.34 (q, 2H); 5.68 (d, 1H); 7.63 (d, 2H); and 8.23 (d, 2H) ppm.

Diastereomer H

IR (KBr disc): 2.88, 5.58, 5.91 and 6.58 microns.
NMR ($CDCl_3$, 250 MHz): 0.04 (s, 3H); 0.07 (s, 3H); 0.83 (s, 9H); 1.26 (d, 3H); 3.08 (b, 1H); 3.46 (c, 4H); 3.79 (dd, 1H); 4.02 (m, 1H); 4.28 (m, 1H); 4.74 (m, 1H); 5.33 (q, 2H); 5.75 (d, 1H); 7.62 (d, 2H); and 8.22 (d, 2H) ppm.

preparation of diastereomers of p-nitrobenzyl (5R, 6S)-6-[(R)-1-hydroxyethyl]-2-(1,1-dioxo-cis-3-hydroxy-4-thiolanyl]thio-2-penem-3-carboxylate The procedure of Preparation A was employed using Diastereomers G and H as starting materials to obtain the corresponding compound of formula XV in 64.2 and 59.7% yield, respectively.

Compound of formula XV derived from Diastereomer G

NMR (DMSO-$d_6$, 250 MHz): 1.18 (d, 3H); 3.34 (m, 2H); 3.52 (m, 2H); 3.94 (dd, 1H); 4.03 (m, 1H); 4.15 (m, 1H); 4.68 (m, 1H); 5.25 (d, 1H); 5.38 (q, 2H); 5.78 (d, 1H); 6.46 (d, 1H); 7.7 (d, 2H); and 8.25 (d, 2H) ppm.

Compound of formula XV derived from Diastereomer H IR (KBr disc): 2.89, 5.62, 6.00, 6.58, and 6.73 microns.
NMR (DMSO-$d_6$, 250 MHz): 1.18 (d, 3H); 3.31 (m, 2H); 3.52 (dd, 1H); 3.74 (dd, 1H); 3.9 (dd, 1H); 4.03 (m, 1H); 4.14 (m, 1H); 4.66 (m, 1H); 5.24 (d, 1H); 5.39 (q, 2H); 5.82 (d, 1H); 6.44 (d, 1H); 7.72 (d, 2H); and 8.25 (d, 2H) ppm.

preparation of diastereomers of sodium (5R, 6S)-6-[(R)-1-hydroxyethyl]-2-(1,1-dioxo-cis-3-hydroxy-4-thiolanyl]thio-2-penem-3-carboxylate The procedure of Example 1 was employed using compounds of formula XV derived from Diastereomers G and H to obtain the corresponding sodium salts of compounds of formula II in 45.6 and 69.6% yield, respectively.

Compound of formula II derived from Diastereomer G

IR (KBr): 2.92, 5.64, and 6.29 microns.
NMR ($D_2O$, 250 MHz): 1.33 (d, 3H); 3.5 (c, 3H); 3.78 (dd, 1H); 3.98 (dd, 1H); 4.26 (c, 2H); 4.62 (m, 1H); and 5.73 (d, 1H) ppm.

Compound of formula II derived from Diastereomer H

IR (KBr): 294, 5.65, and 6.34 microns.
NMR ($D_2O$, 250 MHz): 1.32 (d, 3H); 3.54 (c, 3H); 3.88 (dd, 1H); 3.97 (dd, 1H); 4.27 (c, 2H); 4.63 (m, 1H); and 5.73 (d, 1H) ppm.

EXAMPLE 12

(5R, 6S)-6-[(R)-1-Hydroxyethyl]-2-(cis-1-oxo-3-thiolanyl)thio-3-carboxyl-2-penem Sodium (5R, 6S)-6-[(R)-1-hydroxyethyl]-2-(cis-1-oxo-3-thiolanyl)thio-2-penem-3-carboxylate(3.5 g) was dissolved in 30 ml. water. Ethyl acetate (20 ml.) was added and the pH of the aqueous phase was adjusted to 3.25 with 6N aqueous hydrochloric acid solution. The aqueous phase was separated, cooled to 0° C. and its pH was lowered to 2.6 with 6N aqueous hydrochloric acid solution. After 30 min. the resulting precipitate was filtered, washed with 4 ml. water, 10 ml. diethyl ether, 10 ml. ethyl acetate and dried, yielding 1.77 g. (54% yield.) of the title compound as off-white crystals, m.p. 190° C. (with decomposition).

EXAMPLE 13

2-Methyl-2-propylcarbonyloxymethyl (5R, 6S)-6-[(R)-1-Hydroxyethyl]-2-(cis-1-oxo-3-thiolanyl)thio-2-penem-3-carboxylate A solution of sodium tetrabutylammonium sulfate was prepared by adding 0.168 g. (0.002 mole) sodium bicarbonate to a solution of 0.678 g. (0.002 mole) tetrabutylammonium hydrogen sulfate in 5 ml. water. To this solution, 0.742 g. (0.002 mole) of (5R, 6S)-6-[(R)-1-hydroxyethyl]-2-(cis-1-oxo-3-thiolanyl)-3-carboxyl-2-penem was added and the resulting solution was extracted with 50 ml. chloroform. The aqueous phase was then saturated with sodium sulfate and extracted with two 30 ml. portions of chloroform. The combined chloroform extracts were dried over anhydrous sodium sulfate and concentrated in vacuo to yield the tetrabutylammonium salt of the starting penem as a foam. Chloromethyl pivalate (0.32 ml., 0.0022 mole) was added to a solution of the tetrabutylammonium salt of the penem dissolved in 3 ml. acetone and the reaction mixture was stirred overnight at 25° C. The solution was then diluted with 125 ml. ethyl acetate and the ethyl acetate solution was washed with two 30 ml. portions of water, 25 ml. brine, 30 ml. water and 30 ml. brine, dried over anhydrous sodium sulfate and concentrated in vacuo. The brownish solid was chromatographed on silica gel (300 g.) eluting with 9:1 ethyl acetate-methanol to yield 0.62 g. (66.4% yield) of the title compound as an off-white solid, m.p. 125°–135° C. (with decomposition).

IR (KBr): 2.96 (b), 5.60, 5.69, 5.91 and 6.75 microns.

NMR (CDCl$_3$, 250 MHz): 1.23 (s, 9H); 1.35 (d, 3H); 2.5 (b, 1H); 2.6–2.9 (c, 4H); 3.16 (m, 1H); 3.62–4.0 (c, 3H); 4.25 (m, 1H); 5.7 and 5.72 (2d, 1H); and 5.88 (q, 2H) ppm.

EXAMPLE 14

Using the procedures and materials of Example 13, but employing alkylating agents other than chloromethyl pivalate, the corresponding esters of the title compound of Example 12 was prepared. In Table 1A, R$_1$, the corresponding alkylating agent derivative of R$_1$, infrared spectrum, NMR spectrum and yield are shown. In all cases the infrared spectra were recorded for the potassium bromide disc and the NMR at 250 MHz for the deuterochloroform solutions.

TABLE 1A

| R$_1$ | R$_1$ Derivative | IR (microns) | NMR (ppm) | Yield % |
|---|---|---|---|---|
| 3-phthalidyl | bromide | 2.93 (b), 5.59, 5.85, 5.90 and 6.72 | 1.26 and 1.28 (2d, 3H); 1.88 (b, 1H); 2.56–2.94 (c, 4H); 3.14 (m, 1H); 3.62–3.95 (c, 3H); 4.13 (c, 1H); 5.7 (c, 1H); 7.42 and 7.46 (2S, 1H); 7.58–7.95 (c, 4H). | 58 |
| 5-methyl-2-oxo-1,3-dioxolen-4-yl)-methyl | bromide | 2.9(b), 5.48, 5.6, 5.91 and 6.67 | 1.35 (d, 3H); 2.2 (S, 3H); 2.6–2.95 (C, 5H); 3.16 (m, 1H); 3.64–3.96 (c, 3H); 4.22 (m, 1H); 4.98 (m, 2H); 5.69 and 5.72 (2d, 1H). | 41.3 |
| 1-(methylcarbonyloxy)-1-ethyl | chloride | 2.92 (b), 5.57, 5.68, 5.90 and 6.67 | 1.35 and 1.36 (2d, 3H); 1.54 and 1.55 (2d, 3H); 2.07 and 2.1 (2s, 3H); 2.6–2.9 (c, 5H); 3.14 (m, 1H); 3.62–3.98 (c, 3H); 4.23 (m, 1H); 5.68 (c, 1H); 6.94 (c, 1H). | 44.8 |
| 1-(ethoxycarbonyloxy)-1-ethyl | chloride | 2.94 (b), 5.57, 5.68, 5.91 and 6.68 | 1.32 (c, 6H); 1.57 and 1.58 (2d, 3H); 2.58–2.94 (c, 5H); 3.14 (m, 1H); 3.6–4.0 (c, 3H); 4.23 (c, 3H); 5.67 and 5.70 (2d, 1H); 6.85 (m, 1H). | 67 (esterification proceeded for 96 hours) |

The procedures and materials of Example 13 were employed with (5R, 6S)-6-[(R)-1-hydroxyethyl]-2-(1,1-dioxo-3-thiolanyl)thio-3-carboxyl-2-penem as starting material to obtain the 2-methyl-2-propylcarbonyloxymethyl ester as off-white crystals, mp. 149°–150° C. (with decomposition) in 63.6% yield.

IR (KBr disc): 2.9 (b), 5.64, 5.67, 5.96 and 6.65 microns.

NMR (CDCl$_3$, 250 MHz): 1.24 (s, 9H); 1.37 (d, 3H); 2.15–2.38 (c, 2H); 2.76 (m, 1H); 3.02–3.23 (c, 2H); 3.35 (m, 1H); 3.58 (m, 1H); 3.79 (dd, 1H); 4.0 (c, 1H); 4.27 (m, 1H); 5.72 (d, 1H); and 5.88 (q, 2H) ppm.

PREPARATION A p-Nitrobenzyl (5R, 6S)-6-([(R)-1-Hydroxyethyl]-2-(1,1-dioxo-3-thiolanyl)thio-2-penem-3-carboxylate To a solution of 185 mg. (0.303 mmole) of p-nitrobenzyl (5R, 6S)-6-[(R)-1-t-butyldimethylsilyloxyethyl]-2-(1,1-dioxo-3-thiolanyl)thio-2-penem-3-carboxylate in 6 ml. tetrahydrofuran was added 0.175 ml (3.03 mmole acetic acid and 0.909 ml. (0.909 mmoles) of a 1M solution of tetrabutylammonium fluoride in tetrahydrofuran. After stirring 20 hr. under a nitrogen atmosphere, 50 ml. ethyl acetate was added and the resulting solution was washed with 25 ml. saturated aqueous sodium bicarbonate, 25 ml. water and 25 ml. saturated aqueous sodium chloride. The ethyl acetate solution was then dried over anhydrous sodium sulfate, filtered and concentrated in vacuo. The crude product (138 mg.) was purified by chromatography on silica gel (50 g.), eluting with 60:40 chloroform-ethyl acetate, yielding 72 mg (47.5% yield) of an amorphous solid of the title compound.

The NMR spectrum of a deuterochloroform solution of the title compound showed peaks at 1.35 (d,3H); 1.9–4.4(c, 10H); 5.3(q,2H);5.7(d,1H); 7.5(d,2H); and 8.18 (d,2H)ppm. The infrared spectrum of the title compound in dichloromethane showed absorptions at 5.56, 5.92 and 6.57 microns.

PREPARATION B

The procedures of Preparation A were employed to convert a corresponding compound of formula XIV to one of formula XV wherein R is as indicated in Table 5. For the product, the IR absorption spectra were measured for a dichloromethane solution unless otherwise indicated and the NMR spectral peaks were measured for a deuterochloroform solution unless otherwise indicated.

TABLE 5

| R | IR(microns) | NMR (ppm) | Yield (%) |
|---|---|---|---|
| 3-thiolanyl | 5.56, 5.88 and 6.56 | 1.35 (d,3H); 1.8–4.4 (c,10H); 5.3 (q,2H); 5.65 (d,1H); 7.6 (d,2H); and 8.2 (d,2H). | 51 |
| cis-1-oxo-3-thiolanyl | 5.56, 5.86 and | 1.3 (d,3H); 1.9– | 51 |

TABLE 5-continued

| R | IR(microns) | NMR (ppm) | Yield (%) |
|---|---|---|---|
| (more polar isomer) | 6.56 | 4.38 (c,10H); 5.3 (q,2H); 5.7 (d, 1H); 7.6 (d, 2H); and 8.2 (d, 2H). | |
| trans-1-oxo-3-thiolanyl (less polar isomer) | 5.56, 5.88 and 6.58 | 1.3(d, 3H); 1.86-4.56 (c, 10H); 5.3 (q, 2H); 5.72 (d, 1H); 7.6 (d, 2H); and 8.2 (d, 2H) | 51 |
| 2-(methylsulfinyl)-ethyl | 5.56, 5.9 and 6.55 | 1.35 (d, 3H); 2.65 (S, 3H); 2.9-3.5 (c, 4H); 3.75 (M, 1H); 4.2 (c, 2H); 5.34 (q, 2H); 5.7 (d, 1H); 7.6 (d, 2H); and 8.2 (d,2H). | 67 |
| 2-(methylsulfonyl)-ethyl | 5.57, 5.9 and 6.58 | 1.23 (d, 3H); 3.0 (s, 3H); 3.4 (s, 4H); 3.8 (m, 1H); 4.0-4.8 (c, 2H); 5.36 (q, 2H); 5.8 (d, 1H); 7.74 (d, 2H); and 8.2 (d, 2H). | 85 |
| methylsulfinyl-methyl | 5.57, 5.92 and 6.6 | 1.35 (d, 3H); 2.68 (S, 3H); 3.64-4.45 (c, 5H); 5.3 (q, 2H); 5.7 (d, 1H); 7.56 (d, 2H); and 8.2 (d, 2H). | 65 |
| methylsulfonyl-methyl | 5.6, 5.86 and 6.57 | 1.36 (d,3H); 3.08 (s, 3H); 3.8-4.8 (c, 5H), 5.42 (q, 2H); 5.8 (d, 1H); 7.75 (d, 2H); 8.24 (d, 2H). | 34 |
| 1-oxo-3-thianyl | 5.56, 5.94 and 6.58 | 1.32 (d, 3H); 1.5-4.38 (c, 12H); 5.3 (q, 2H); 5.7 (d, 1H); 7.6 (d, 2H); and 8.2 (d, 2H). | 26 |
| 1,1-dioxo-3-thianyl | 5.56, 5.8 and 6.55 | 1.3 (d, 3H); 1.76-4.4 (c, 12H); 5.3 (q, 2H); 5.68 (d, 1H); 7.6 (d, 2H); and 8.2 (d, 2H). | 47 |
| 3-thietanyl | 5.56, 5.88 and 6.56 | 1.3 (d, 3H); 3.38 (c, 4H); 3.68 (m, 1H); 4.22 (m, 1H); 4.8 (m, 1H); 5.3 (q, 2H); 5.6 (d, 1H); 7.55 (d, 2H); and 8.16 (d, 2H). | 74 |
| 4-thianyl | 3424, 1773 and 1688 cm$^{-1}$ | 1.39 (3H, d); 1.8-2.0 (3H, m); 2.3-2.5 (2H, m); 2.6-2.85 (4H, m); 3.23 (1H, tt); 3.77 (1H, dd); 4.28 (1H, m); 5.23 (1H, d); 5.49 (1H, d); 5.68 (1H, d); 7.64 (2H, d); and 8.22 (2H, d). (250 MHz) | 90 |
| 1,1-dioxo-4-thianyl | 3530, 1772, 1681, 1510, 1344, 1290, and 1115 cm$^{-1}$ (KBr disc) | 1.15 (3H, d, J = 6.2 Hz); 1.95-2.15 (2H, m); 2.3-2.55 (2H, m); 3.05-3.5 (4H, m); 3.58 (1H, m); 3.89 (1H, dd, J = 5.8, 1.4 Hz); 4.00 (1H, m); 5.23 (1H(OH),d, J = 4.6 Hz); 5.28 (1H, D, Jgem = 14Hz); 5.43 (1H, d, Jgem = 14 Hz); 5.77 (1H, d, J = 1.4 Hz); 7.68 (2H, d, J = 8.6 Hz); and 8.23 (2H, d, J = 8.6 Hz. (DMSOd$_6$ 250 MHz | 77 |
| cis-1-oxo-4-thianyl (m.p. 206-208° C.) | 3435, 2940, 2919, 2862 1768, 1686, 1609, 1504 1378, 1343, 1324, 1298, 1244, 1204 1129, 1043 1016, 1005, 994, and 730 cm$^{-1}$. (KBr) | 1.17 (3H, d, J = 6.3 Hz); 1.95-2.3 (4H, m); 2.7-3.0 (4H, m); 3.43 (1H, tt, J = 11, 7 Hz); 3.88 (1H, dd, J=5.8, 1.3 Hz): 4.01 (1H qdd, J = 6.3, 5.8, 4.6 Hz); 5.21 (1H, d, J = 4.6 Hz); 5.29 & 5.44 (2H, both d, J$_{AB}$ = 14.0 Hz); 5.77 (1H, d, J = 1.3 Hz); 7.69 (2H, d, J = 8.6 Hz); and 8.24 (2H, d, J = 8.6 Hz) (DMSO-d$_6$, 250 MHz) | 92 |
| trans-1-oxo-4-thianyl | | 1.18 (3H, d, J = 6.2 Hz); 1.8-1.95 (2H, m); 2.45-2.6 (2H, m); 2.79 (2H, m); 3.04 (2H, m); 3.62 (1H, m); 3.90 (1H, dd, J = 5.7, 1.3 Hz); 4.02 (1H, m); 5.23 (1H, broad d, J = 14.0 Hz); 5.29 & 5.45 (2H, both d, J$_{AB}$ = 14.0 Hz); 5.78 (1H, d, J = 1.3 Hz); 7.70 (2H, d, J = 8.7 Hz); and 8.25 (2H, d, J = 8.7 Hz) (DMSO-d$_6$, | 92 |

TABLE 5-continued

| R | IR(microns) | NMR (ppm) | Yield (%) |
|---|---|---|---|
| cis-1-oxo-3-thianyl | 5.57, 5.91 and 6.58 | 250 MHz) 1.35 (d, 3H); 1.4–3.96 (c, 11H); 4.18 (m, 1H); 5.31 (q, 2H); 5.69 (d, 1H, 7.58 (d, 2H); and 8.22 (d, 2H) | 83.4 |
| trans-1-oxo-3-thianyl | 5.57, 5.9 and 6.58 | 1.35 (d, 3H); 1.4–4.43 (c, 1H); 5.3 (q, 2H); 5.7 (d, 1H); 7.55 (d, 2H); and 8.14 (d, 2H). | 58.5 |

PREPARATION C p-Nitrobenzyl (5R, 6S)-6-[(R)-1-t-Butyldimethylsilyloxymethyl]-2-methyl-sulfinylmethylthio-2-penem-3-carboxylate Sodium methoxide (27 mg. 0.5 mmole) was added to a solution of 76 mg. (0.5 mmole) methylsulfinylmethyl thioacetate in 5 ml. anhydrous ethanol cooled to −40° C. under a nitrogen atmosphere. After 90 min. at −40° C., a solution of 300 mg. (0.5 mmole) of p-nitrobenzyl (5R, 6S)-6-[(R)-1-t-butyldimethylsilyloxy]ethyl-2-ethyl-sulfinyl-thio-2-penem-3-carboxylate in 5 ml. tetrahydrofuran which had been cooled to −50° C. was added. The resulting solution was stirred at −40° C. for 65 min., then 0.029 ml. (0.5 mmole) acetic acid was added and the solution was concentrated in vacuo. The residue was dissolved in 50 ml. ethyl acetate and the resulting solution was washed sequentially with 25 ml. saturated aqueous sodium bicarbonate solution, 25 ml. water and 25 ml saturated aqueous sodium chloride solution. The ethyl layer was dried with anhydrous sodium sulfate and concentrated in vacuo. Chromatography of the crude title product (290 mg.) on silica gel (85 g.), eluting with 80:20 chloroform-ethyl acetate yielded 120 mg. (42% yield) of product as a viscous gum.

The infrared spectrum of a dichloromethane solution of the title compound showed absorptions at 5.58, 5.9 and 6.6 microns. The NMR spectrum of a deuterochloroform solution of the title compound showed peaks at 0.03(s,3H);0.05(s, 3H)0.83(s, 9H); 1.24(d, 3H);2.7 (s, 3H); 3.7–4.22(c, 4H); 5.28 (q, 2H); 5.68(d, 1H); 7.56(d, 2H); and 8.18(d, 2H)ppm.

PREPARATION D

The procedure of Preparation C was employed to prepare compounds of formula XIV from the corresponding thioacetate wherein R is as indicated in Table 6. The infrared spectra of the products of formula XIV were measured in dichoromethane solution and the NMR spectra were measured in deuterochloroform unless otherwise indicated.

TABLE 6

| R | IR (microns) | NMR (ppm) | Yield (%) |
|---|---|---|---|
| methylsulfonyl-methyl | 5.56, 5.88 and 6.54 | 0.1 (s, 6H); 0.9 (s, 9H); 1.22 (d, 3, H); 2.9 (s, 3H); 3.64 (m, 1H); 4.16 (c, 3H); 5.2 (q, 2H); 5.57 (d, 1H); 7.42 (d, 2H); and 8.06 (d, 2H). | 27 |
| 2-(methylsulfinyl)-ethyl | 556, 5.92 and 6.56 | 0.06 (S, 3H); 0.1 (S, 3H); 0.85 (S, 9H); 1.26 (d, 3H); 2.66 (3H); 2.86–3.54 (C, 4H); 3.74 (M, 1H); 4.2 (M, 1H); 5.3 (q, 2H); 5.7 (d, 1H); 7.6 (d, 2H); and 8.2 (d, 2H). | 26 |
| 2-(methylsulfonyl)-ethyl | 5.56, 5.9 and 6.58 | 0.03 (s, 3H); 0.06 (s, 3H); 0.8 (s, 9H); 1.23 (d, 3H); 2.98 (s, 3H); 3.36 (s, 4H); 3.64 (m, 1H); 4.2 (m, 1H); 5.28 (q, 2H); 5.68 (d, 1H); 7.57 (d, 2H); and 8.18 (d, 2H). | 34 |
| 3-thiolanyl | 5.56, 5.92 and 6.56 | 0.02 (s, 3H); 0.06 (s, 3H); 0.82 (s, 9H); 1.25 (d, 3H); 1.8–4.4 (c, 9H); 5.3 (q, 2H) 5.66 (d, 1H); 7.6 (d, 2H); and 8.2 (d, 2H). | 41 |
| 1-oxo-3-thianyl | 5.57, 5.95 and 6.58 | 0.06 (s, 3H); 0.08 (S,3H); 0.88 (s, 9H); 1.26 (d, 3H); 1.5–4.4 (c, 11H); 5.3 (q, 2H); 5.7 (d, 1H); 7.6 (d, 2H); and 8.2 (d, 2H). | 22 |
| 1,1-dioxo-3-thianyl | 5.56, 5.88 and 6.54 | 0.03 (s, 3H); 0.06 (s, 3H); 0.82 (s, 9H); 1.24 (d, 3H); 1.8–4.42 (c, 11H); 5.3 (q, 2H); 5.7 (d, 1H); 7.6 (d, 2H); and 8.2 (d, 2H). | 42 |
| 3-thietanyl | 5.56, 5.88 and 6.56 | 0.03 (s, 3H); 0.06 (s, 3H); 0.82 (s, 9H); 1.24 (d, 3H); 3.4 (c, 4H); 3.7 (m, 1H); 4.23 (m, 1H); 4.85 (m, 1H); 5.3 (q, 2H); 5.63 (d, 1H); 7.6 (d, 2H); and 8.2 (d, 2H). | 28 |
| 4-thianyl | | 0.13 (6H, s); 0.92 (9H, s); 1.40 (3H, d, J = 7 Hz); 1.8–2.9 (8H, m); 3.27 (1H, m); 3.75 (1H, dd, J = 4 1.5 Hz); 4.3 (1H, m), 5.18 (1H, d, $J_{AB}$ = 13 Hz); 5.48 (1H, d, $J_{AB}$ = 13 Hz); | 37 |

TABLE 6-continued

| R | IR (microns) | NMR (ppm) | Yield (%) |
|---|---|---|---|
| 1,1-dioxo-4-thianyl | | 5.67 (1H, d, J = 1.5 Hz); 7.60 (2H, d, J = 8 Hz); and 8.18 (2H, d, J = 8 Hz). 0.13 (3H, s); 0.17 (3H, s); 0.93 (9H, s); 1.33 (3H, d, J = 6 Hz); 2.4–3.4 (8H, m); 3.6 (1H, m); 3.80 (1H, dd); 4.3 (1H, m); 5.17 (1H, d, J = 13 Hz); 5.47 (1H, d, J = 13 Hz); 5.69 (1H, d, J = 1 Hz); 7.57 (2H, d, J = 8 Hz); and 8.15 (2H, d, J = 8 Hz). | 60 |
| cis-1-oxo-4-thianyl | 2924, 2489 1782, 1682, 1606, 1511, 1487, 1328, 1196, 1110, 1055, 997, and 830 cm$^{-1}$ (KBr disc) | 0.04 (3H, s); 0.07 (3H, s); 0.83 (9H, s); 1.25 (3H, d, J = 6.3 Hz); 2.1–2.3 (2H, m); 2.45–2.7 (4H, m); 3.05–3.2 (2H, m); 3.27 (1H, m); 3.73 (1H, dd, J = 4.2, 1.4 Hz); 4.27 (1H, qd, J = 6.3, 4.2 Hz); 5.21 & 5.42 (2H, both d, J$_{AB}$ = 13.7 Hz); 5.66 (1H, d, J = 1.4 Hz); 7.62 (2H, d, J = 8.7 Hz); and 8.21 (2H, d, J = 8.7 Hz). (250 MHz). | 68 |
| trans-1-oxo-4-thianyl | | 0.10 (6H, s); 0.87 (9H, s); 1.28 (3H, d, J = 6 Hz); 1.7–2.3 (2H, m); 2.5–3.1 (6H, m); 3.6 (1H, m); 3.74 (1H, dd, J = 4, 1.5 Hz); 4.2 (1H, m); 5.13 (1H, d, J$_{AB}$ = 13 Hz); 5.45 (1H, d, J$_{AB}$ = 13 Hz); 5.67 (1H, d, J = 1.5 Hz); 7.57 (2H, d, J = 8 Hz); and 8.15 (2H, d, J = 8 Hz). | 41 |
| cis-1-oxo-3-thianyl | 5.58, 5.9 and 6.58 | 0.04 (s, 3H); 0.06 (s, 3H); 0.82 (s, 9H); 1.24 (d, 3H); 1.3–3.98 (c, 10H); 4.23 (m, 1H); 5.24 (q, 2H); 5.64 (d, 1H); 7.5 (d, 2H); and 8.15 (d, 2H). | 45.5 |
| trans-1-oxo-3-thianyl | 5.58, 5.92 and 6.58 | 0.03 (s, 3H); 0.07 (s, 3H); 0.83 (s, 9H); 1.22 (d, 3H); 1.4–3.56 (c, 8H); 3.7 (m, 1H); 3.78–4.46 (c, 2H); 5.26 (q, 2H); 5.63 (d, 1H); 7.52 (d, 2H); 8.12 (d, 2H). | 41.3 |

PREPARATION E p-Nitrobenzyl (5R, 6S)-6-[(R)-1-t-Butyldimethylsilyloxyethyl]-2-(1-oxo-3-thiolanyl)thio-2-penem-3-carboxylate Sodium methoxide (30 mg., 0.552 mmole) was added to a solution of 100 mg (0.552 mmole)1-oxo-3-(methylcarbonylthio)-thiolane in 5 ml. anhydrous ethanol cooled to −30° C. under a nitrogen atmosphere. After 75 min. at −30° C., a solution of 330 mg. (0.552 mmole) of p-nitrobenzyl (5R, 6S)-6-[(R)-1-t-butyldimethylsilyloxyethyl]-2-ethylsulfinyl-2-penem-3-carboxylate in 5 ml. tetrahydrofuran which had been cooled to −50° C. was added. The resulting solution was stirred at −35° to −30° C. for 60 min., then 0.032 ml. (0.552 mmole) acetic acid was added and the solution was concentrated in vacuo. The residue was dissolved in 50 ml. ethyl acetate and the solution was washed sequentially with 25 ml. saturated aqueous sodium bicarbonate solution, 25 ml. water and 25 ml. saturated aqueous sodium chloride solution. The ethyl acetate layer was dried over anhydrous sodium sulfate and concentrated in vacuo. Chromatography of the crude product (315 mg) on silica gel (100 g), eluting with 92.5:7.5 ethyl acetate-methanol yielded 53 mg (16%) of the less polar title compound isomer and 65 mg. (20%) of the more polar title compound sulfoxide isomer.

The more polar isomer of the title compound had an infrared spectrum, for a dichloromethane solution, with absorptions at 5.56, 5.92 and 6.58 microns, and an NMR spectrum, for a deuterochloroform solution, with peaks at 0.03(3H);0.08(3H); 0.82(s,9H); 1.24(d, 3H); 1.9–4.4 (c,9H); 5.28(q, 2H); 5.68 (d, 1H); 7.6 (d, 2H); and 8.2 (d, 2H)ppm.

For the less polar isomer of the title compound, the infrared spectrum, for a dichlormethane solution, had absorptions at 5.57, 5.92 and 6.57 microns, and NMR spectrum, for a deuterochloroform solution, had peaks at 0.04(s,3H); 0.08(s,3H); 0.8(s,9H); 1.23(d, 3H); 1.8–4.56(c, 9H); 5.26(q, 2H); 5.66 (d, 1H); 7.6 (d, 2H); and 8.2 (d, 2H)ppm.

PREPARATION F p-Nitrobenzyl (5R, 6S)-6-[(R)-1-t-butyldimethylsilyloxyethyl]-2-(1,1-dioxo-3-thiolanyl)thio-2-penem-3-carboxylate To a solution of 3-sulfolanethiol (1,1-dioxo-3-thiolanyl mercaptan) (76 mg., 0.5 mmole) in 5 ml. ethanol cooled to −35° C. under a nitrogen atmosphere was added 27 mg. (0.5 mmole) of sodium methoxide. After 45 min. at −35° C. a solution of 300 mg. (0.5 mmole) of p-nitrobenzyl (5R, 6S)-6-[(R)-1-t-butyldimethylsilyloxyethyl]-2-ethylsulfinyl-2-penem-3-carboxylate in 5 ml. anhydrous tetrahydrofuran which had been cooled to −50° C. was added. The resulting solution was stirred for 60 min. at −35° C., then 0.029 ml. (0.5 mmole) acetic acid was added. The solution was concentrated in vacuo and the residue was dissolved in 50 ml. ethyl acetate. The ethyl acetate solution was washed sequentially with 25 ml. saturated aqueous sodium bicarbonate solution, 25 ml. water and 25 ml. saturated aqueous sodium chloride solution, dried over anhydrous sodium sulfate, filtered and concentrated in vacuo. The crude product (285 mg.) was purified by chromatography on silica gel (100 g.), eluting with 95:5 chloromethyl acetate to yield 185 mg. (60% yield) of the title compound as a gum.

A dichloromethane solution of the title compound had an infrared spectrum with absorptions at 5.57, 5.88 and 6.58 microns. The NMR spectrum for a deuterochloroform solution of the title compound showed peaks at 0.06(s,3H); 0.1(s,3H); 0.85(s,9H); 1.26(d,3H); 2.0–4.4(c, 9H); 5.32 (q, 2H); 5.72(d, 1H); 7.6 (d, 2H); and 8.2 (d, 2H)ppm.

PREPARATION G p-Nitrobenzyl (5R, 6S)-6-[(R)-1-t-Butyldimethylsilyloxyethyl]-2-ethylsulfinyl-2-penem-3-carboxylate A solution of 970 mg. (4.78 mmoles, 85% purity) m-chloroperbenzoic acid in 25 ml. methylene chloride was added to a solution of 2.5 g. (4.78 mmoles) of p-nitrobenzyl (5R, 6S)-6-[(R)-1-t-butyldimethylsilyloxyethyl]-2-ethylthio-2-penem-3-carboxylate in 125 ml. methylene chloride cooled to −20° C. under a nitrogen atmosphere. The mixture was stirred at −20° C. for 3 hr., then washed sequentially with two 70 ml. portions of saturated aqueous sodium bicarbonate solution, 70 ml. water and 70 ml. saturated aqueous sodium chloride solution. The methylene chloride solution was dried with anhydrous sodium sulfate and concentrated in vacuo to a yellow foam of the title compound (2.2 g., 86% yield).

The infrared spectrum of the title compounds as a dichloromethane solution had absorptions at 5.54, 5.86 and 6.53 microns. The NMR spectrum of the title compound as a deuterochloroform solution had peaks at 0.06, 0.08, 0.1 and 0.12 (4s, total 6H); 0.8(s, 9H); 1.12–1.58 (m, 6H); 3.1 (m, 2H); 3.86(m, 1H), 4.3(m, 1H), 5.3 (m, 2H); 5.67 and 5.78 (2d, total 1H); 7.54(d, 2H); and 8.18 (d, 2H)ppm.

PREPARATION H p-Nitrobenzyl (5R, 6S)-6-[(R)-1-t-Butyldimethylsilyloxyethyl]-2-ethylthio-2-penem-3-carboxylate p-Nitrobenzyl oxalyl chloride (5.85 g. 0.024 mole) was added to a mixture of 7.3 g (0.02 mole) (3-[(R)-1-t-butyldimethylsilyloxyethyl]-4-ethylthio(thiocarbonyl) thio-2-oxo-azetidine and 4.8 g. (0.048 mole) calcium carbonate in 70 ml. methylene chloride cooled to 10° C. under a nitrogen atmosphere. A solution of 4.17 ml. (0.024 mole) disopropylethylamine in 20 ml. methylene chloride was added dropwise at a rate to keep the temperature below 12° C. The mixture was stirred for 60 min. at 10° C., then washed with two 50 ml. portions of ice cold water, dried over anhydrous sodium sulfate and concentrated in vacuo to a viscous oil. The resulting crude p-nitrobenzyl (3-alpha-t-butyldimethylsilyloxyethyl-2-oxo-azetidinyl)oxoacetate was dissolved in 300 ml. ethanol-free chloroform and the resulting solution was refluxed under nitrogen while a solution of 6.85 ml. (0.04 mole) triethylphosphite in 50 ml. ethanol-free chloroform was added dropwise over 2 hr. The resulting solution was refluxed for 16 hr., then concentrated in vacuo. The residue was chromatographed on silica gel (800 g.), eluting with 95:5 toluene-ethyl acetate to yield 5.5 g. (53% yield) of the title compound as a yellow foam.

The infrared spectrum of the title compound as a dichloromethane solution had absorptions at 5.56, 5.89 and 6.54 microns. The NMR spectrum of the title compound as a deuterochloroform solution had peaks at 0.07(s,3H); 0.1(s,3H); 0.85(s,9H); 1.12–1.53(m,6H); 2.97(q,2H); 3.7(m,1H); 4.25(m,1H); 5.3(q,2H); 5.63 (d,1H); 7.38(d,2H); and 8.18(d,2H)ppm.

The NMR spectrum of the intermediate 4-ethylthio (thiocarbonyl)thio azetidine as a deuterochloroform solution had peaks at 0.06(s,6H); 0.8(s,9H); 1.14–1.62(m,6H); 3.14–3.63(m,3H); 4.33(m,1H); 5.16(s,2H); 6.7(d,1H); 7.5(d,2H); and 8.17(d,2H)ppm.

PREPARATION I

3-[(R)-1-t-Butyldimethylsilyloxyethyl]-4-ethylthio(thiocarbonyl)thio-2-oxo-azetidine Ethanethiol (8.5 ml. 0.115 mole) was added to a solution of 4.18 g. (0.104 mole) sodium hydroxide in 250 ml. water cooled to 0°–5° C. under a nitrogen atmosphere. After 15 min. 7.73 ml. (0.12 mole) carbon disulfide was added and the mixture was stirred at 0°–5° C. for 35 min. A solution of 15.0 g. (0.0522 mole) 4-acetoxy-3-[(R)-1-t-butyldimethylsilyloxyethyl]-2-azetidinone in 500 ml. methylene chloride was added and the mixture was stirred vigorously at room temperature for 24 hr. The aqueous phase was separated and extracted with two 150 ml. portions of methylene chloride. The combined methylene chloride fractions were washed with two 200 ml. portions of water and 200 ml. saturated aqueous sodium chloride solution, dried over anhydrous sodium sulfate and concentrated in vacuo. The crude title product (18 g.) was chromatographed on silica gel (500 g.), eluting with 99:1 chloroform-ethyl acetate to yield 9.1 g. (48% yield) of title trithiocarbonate as a yellow foam.

The infrared spectrum of the title compound in dichloromethane solution had absorptions at 5.62 and 9.2 microns. The NMR spectrum of a deuterochloroform solution of the title compound had peaks at 0.08(s,6H); 0.8(s,9H); 1.02–1.5(m,6H); 3.0–3.48(m,3H); 4.12(m,1H); 5.54(d,1H); and 6.57(b,1H)ppm.

PREPARATION J

3-Methylcarbonylthio-thiolane

Methanesulfonyl chloride (0.8 ml. 0.01 mole) was added to a solution of 1.04 g. (0.01 mole) tetrahydrothiophen-3-ol and 2.44 g. (0.02 mole) 4-dimethylaminopyridine in 40 ml. methylene chloride cooled to 0° C. under nitrogen. After stirring for 1.5 hr. at 0° C. and 2 hr. at room temperature the solution was washed with 30 ml. 1N aqueous hydrochloric acid solution, 30 ml. water and 30 ml. saturated sodium chloride solution, dried over anhydrous sodium sulfate and concentrated in vacuo to an oil (1.6 g., 88% yield) which was 3-methylsulfonyloxy-thiolane.

A mixture of 1.6 g. (8.8 mmole) of crude 3-methylsulfonyloxy-thiolane and 1.5 g. (8.8 mmole) potassium thioacetate in 40 ml. acetone was refluxed under nitrogen for 20 hr. The mixture was then concentrated in vacuo and the residue was partitioned between 40 ml. ethyl acetate and 40 ml. water. The ethyl acetate layer was separated and washed with 30 ml. water and 30 ml. saturated sodium chloride solution, dried with anhydrous sodium sulfate and concentrated in vacuo. The crude product was chromographed on silica gel eluting with methylene chloride to yield 740 mg. (52%) of the title compound.

The NMR spectrum of the title compound in deuterochloroform had peaks at 2.35(s,3H); 1.6–3.4(c,6H); and 4.1(m,1H)ppm.

PREPARATION K

The same procedures employed in Preparation J in reacting 3-methylsulfonyloxythiolane with potassium thioacetate were employed with both 3-chlorothiane and 2-(methylthio)ethyl chloride and potassium thioacetate to obtain the corresponding methylcarbonylthio derivatives in 33 and 100% yield, respectively.

The NMR spectrum of 3-methylcarbonylthio-thiane in deuterochloroform had peaks at 2.36(s,3H); and 1.4–3.68(c,9H)ppm.

PREPARATION L (Methylcarbonylthio)(methylsulfonyl)methane m-Chloroperbenzoic acid (3.0 g., 14.7 mmoles,85% pure) was added to a solution of 1.0 g. (7.34 mmole) (methylcarbonylthio)(methylthio)methane in 50 ml. methylene chloride cooled to 0° C. After stirring at room temperature for 20 hr. the solution was washed with two 30 ml. portions of saturated aqueous sodium bicarbonate solution and 30 ml. saturated aqueous sodium chloride solution, dried (anhydrous sodium sulfate) and concentrated in vacuo. The crude product was purified by column chromatography on silica gel, eluting with ethyl acetate to yield 740 mg. (60% yield) of the title compound as a thick gum.

The NMR spectrum of a deuterochloroform solution of the title compound had peaks at 2.5(s,3H); 2.94(s,3H); and 4.4(s,2H)ppm.

PREPARATION M

The procedures of Preparation L were employed to prepare 3-methylcarbonylthio-1,1-dioxo-thiane in 32% yield and 2-(methylcarbonylthio)-1-methylsulfonyl)ethane in 55% yield.

The NMR spectrum of the 1,1-dioxo-thiane product in deuterochloroform had peaks at 2.36(s,3H); and 1.7–3.37(c,9H)ppm.

PREPARATION N 2-(Methylcarbonylthio)-1-(methylsulfinyl)ethane m-Chloroperbenzoic acid (2.03 g., 0.01 mole, 85% pure) was added to a solution of 1.5 g (0.01 mole) 2-(methylcarbonylthio)-1-(methylthio)ethane in 40 ml. methylene chloride cooled to −10° C. After stirring at −10° for 2 hr., the solution was washed with two 30 ml. portions of saturated aqueous sodium bicarbonate solution, 30 ml. water and 30 ml. saturated aqueous saturated sodium chloride solution, dried with anhydrous sodium sulfate and concentrated in vacuo. The crude product was purified by column chromatography on silica gel, eluting with 10:1 ethyl acetate-methanol to yield 680 mg. (38% yield) of the title compound as an amorphous solid.

The NMR spectrum of the title compound in deuterochloroform had peaks at 2.4(s,3H); 2.68(s,3H); and 2.76–3.46(c,4H)ppm.

PREPARATION O

The procedures of Preparation N were employed to prepare 3-methylcarbonylthio-1-oxo-thiolane in 42% yield, 3-methylcarbonylthio-1-oxo-thiane in 91% yield and (methylcarbonylthio)-(methylsulfinyl)methane in 32% yield.

The NMR spectrum of the 1-oxo-thiolane product in deuterochloroform had peaks at 2.36(s,3H); and 1.77–4.76(c,7H)ppm.

The NMR spectrum of the 1-oxo-thiane product in deuterochloroform had peaks at 2.36(s,3H); and 1.6–3.4(c,9H)ppm.

The NMR spectrum of (methylcarbonylthio)(methylsulfinyl)methane in deuterochloroform had peaks at 2.5(S,3H);2.94(S,3H); and 4.4(S,2H)ppm.

The procedures of Preparation N were employed to prepare 1,1-dioxo-4-methylcarbonylthiothiane in 43% yield from 4-methylcarbonylthiothiane and 2 equivalents of m-chloroperbenzoic acid. Purification was by column chromatography on silica gel, eluting with 1:1 ethyl acetate: hexane. Analysis: Calculated for $C_7H_{12}O_3S$: C, 40.37, H, 5.81; Found: C, 40.62, H, 5.58. The NMR spectrum of deuterochloroform solutionof the product had peaks at 2.15–2.5 (4H, m); 2.36 (3H, s); 3.02–3.2 (4H, m); and 3.74 (1H, tt, J=8, 4 Hz) ppm.

The infrared spectrum of a potassium bromide disc of the product had absorptions at 1687, 1291 and 1116 $cm^{-1}$.

Also, the procedures of Preparation N were employed to prepare 1-oxo-4-p-methylphenylsulfonyloxythiane from 4-p-methylphenylsulfonyloxythiane. The resulting cis and trans isomers were separated by column chromatography on silica gel eluting with 3 percent methanol/ethyl acetate. The cis-1-oxo-4-p-methylsulfonyloxythiane isomer was more polar. A NMR spectrum (250 MHz) of a deuterochloroform solution of the cis-isomer had peaks at 2.0 (2h, m); 2.48 (2H, m); 2.50 (3H, s); 2.75 (2H, dddd); 3.07 (2H, ddd); 4.67 (1H, tt, J=8.3, 3.4 Hz); 7.41 (2H, d, J=8 Hz); and 7.85 (2H, d, J=8 Hz) ppm.

PREPARATION P

3-Chlorothiane p-Toluenesulfonyl chloride (857 mg. 4.5 mmole) was added to a solution of 530 mg. (4.5 mmole) tetrahydrothiopyran-3-ol and 1.1 g. (9 mmole) 4-dimethylaminopyridine in 30 ml. methylene chloride cooled to 0° C. under nitrogen. The solution was stirred 20 hr. at room temperature, then washed with two 30 ml. portion of 1N aqueous hydrochloric acid solution, 30 ml. water and 30 ml. saturated sodium chloride solution, dried with anhydrous sodium sulfate and concentrated in vacuo to obtain 400 mg., 33% yield, of crude title compound.

PREPARATION Q p-Nitrobenzyl (5R, 6S)-6-[(R)-1-hydroxyethyl]-2-(2-oxo-1,3-dithiolan-4-ylmethyl)thio-2-penem-3-carboxylate A solution of 410 mg p-nitrobenzyl (5R, 6S)-6-[(R)-1-t-butyldimethylsiloxyethyl]-2-(2-oxa-1,3-dithiolan-4-ylmethyl)thio-penem-3-carboxylate in 20 ml of tetrahydrofuran was treated with 0.383 ml of glacial acetic acid and 2.0 ml of 1M tetrabutylammonium fluoride solution. This solution was stirred at room temperature for about 24 hours. The solvent was then removed in vacuo and the residues were dissolved in ethyl acetate. This solution was washed with dilute, aqueous sodium bicarbonate, water and brine and was then dried over anhydrous sodium sulfate, filtered and evaporated. The product was further purified by columm chromatography on silica gel using 1:1 hexane/ethyl acetate and neat ethyl acetate as eluents.

NMR(CDCl$_3$/DMSO-d$_6$): 1.23(3H,d,J=6); 2.92–3.25(2H,m); 3.42–3.67 (4H,m); 5.2(2H,s); 5.30(1H,d,J=2); and 7.83 (4H,d of d) ppm.

IR (CH$_2$Cl$_2$):1792 cm$^{-1}$.

PREPARATION R p-Nitrobenzyl (5R, 5S)-6-[(R)-1-t-Butyldimethylsiloxyethyl]-2-(2-oxo-1,3-dithiolan-4-ylmethyl)thio-2-penem-3-carboxylate A solution of 0.500 g of 4-mercaptomethyl-1,3-di-thiolane-2-one in 50 ml dichloromethane was cooled to 0° C. and then was treated with 0.640 ml of diisopropylethylamine. After 1 hour at 0°–5° C., the solution was added to a solution of 0.307 g. p-nitrobenzyl (5R, 6S)-6-[(R)-1-t-butyldimethylsiloxyethyl]-2-ethylsulfinyl-2-penem-3-carboxylate in 20 ml of dichloromethane at 0-5° C. The reaction mixture was stirred at 0°-5° C. for 1 hour and was then washed sequentially with water and brine and was then dried with anhydrous sodium sulfate. After filtration, the solution was evaporated to a gum which was triturated with 1:1 hexane/ethyl acetate to afford the product as a pale yellow, amorphous solid.

NMR (CDCl$_3$;60 MH$_z$): 0.05(3H,s); 0.08(3H,s), 0.83(9H,s), 1.23(3H,d,J=6; 3.28–3.52 (2H,m); 3.67–3.92 (2H,m); 4.02–4.67 (2H,m); 5.30 (2H,d,J=4); 5.68 (1H,S); and 7.8 (4H, d of d) ppm.

IR(CH$_2$Cl$_2$):1792cm$^{-1}$.

PREPARATION S p-Nitrobenzyl (5R, 6S)-6-[(R)-1-Hydroxyethyl]-2-[(cis)-1-oxo-3-thiolanyl]thio-2-penem-3-carboxylate To a solution of 20.1 g (0.0337 mole) p-nitrobenzyl (5R, 6S)-6-[(R)-1-t-butyldimethylsilyloxyethyl]-2-[(cis)-1-oxo-3-thiolanyl]thio-2-penem-3-carboxylate in 50 ml. anhydrous tetrahydrofuran was added 19.9 ml. acetic acid and 118.8 ml of a 1M solution of tetrabutylammonium fluoride in tetrahydrofuran. After stirring overnight at room temperature under nitrogen the solution was concentrated in vacuo. The residue was dissolved in 500 ml. ethyl acetate and the resulting solution was washed with three 200 ml portions of water. The product began to crystallize out of the water extracts and ethyl acetate layer so crystallization was allowed to proceed to completion (30 min). The crystalline material was filtered, washed with water and ethyl acetate and then slurried in 200 ml. ethyl acetate and filtered to yield 12.03 g (74% yield) of crystalline product. The ethyl acetate and aqueous extracts were combined and the ethyl acetate layer was washed with 300 ml. saturated aqueous sodium bicarbonate solution, 200 ml. water and 200 ml. brine, dried over anhydrous sodium sulfate and concentrated in vacuo to yield 4.6 g of less pure product. This material was recrystallized from ethyl acetate to yield 3.0 g more of product, total yield 92.2%, m.p. 122°–125° C.

The NMR spectrum (250 MHz) of a deuterochloroform solution of the title compound had peaks at 1.37 (d, 3H); 2.57–2.95 (c, 4H); 3.15 (c, 1H); 3.62–3.97 (c, 3H); 4.26 (m, 1H); 5.34 (q, 2H); 5.72 and 5.74 (2d, 1H); 7.63 (d, 2H); and 8.23 (d, 2H) ppm.

The infrared spectrum of a dichloromethane solution of the title compound had absorptions at 5.56, 5.86 and 6.56 microns.

The corresponding trans isomer of the title compound was prepared in 75% yield, m.p. 178.5°–180° C., using the procedures for the cis isomer with p-nitrobenzyl (5R, 6S)-6-[(R)-1-t-butyldimethylsilyloxyethyl]-2-[(trans)-1-oxo-3-thiolanyl]thio-2-penem-3-carboxylate as the starting material.

The NMR spectrum of a deuterochloroform solution of the trans isomer had peaks at 1.4 (d, 3H); 2.22 (c, 1H); 2.62 (c, 1H); 2.8 (m, 1H); 3.04 (c, 2H); 3.18 (c, 1H); 3.52 (m, 1H); 3.83 (m, 1H); 4.27 (c, 1H); 4.43 (c, 1H); 5.36 (q, 2H); 5.76 (d, 1H); 7.64 (d, 2H); and 8.24 (d, 2H) ppm.

The infrared spectrum of a dichloromethane solution of the trans isomer had absorptions at 5.56, 5.88 and 6.58 microns.

PREPARATION T p-Nitrobenzyl (5R, 6S)-6-[(R)-1-t-Butyldimethylsilyloxyethyl]-2-[(cis)-1-oxo-3-thiolanyl]thio-2-penem-3-carboxylate A solution of sodium ethoxide in ethanol (57.5 ml. of 1M solution, 0.0575 mole) was added to a mixture of 10.68 g (0.06 mole) cis-3-methylcarbonylthio-1-oxo-thiolane in 110 ml. absolute ethanol cooled to −30° C. under nitrogen. The resulting solution was stirred at −30° C. for 2 hr. then cooled to −60° C. To this cooled solution was added a solution of 32.4 g (0.06 mole) of p-nitrobenzyl (5R, 6S)-6-[(R)-1-t-butyldimethylsilyloxyethyl]-2-ethylsulfinyl-2-penem-3-carboxylate in 200 ml. tetrahydrofuran which had been cooled to −60° C. The resulting solution was stirred at −60° C. for 1 hr. then a solution of 10 ml. acetic acid in 20 ml tetrahydrofuran was added and the resulting solution was allowed to warm to room temperature and concentrated in vacuo. The residue was dissolved in 500 ml. ethyl acetate and the solution was washed with seven 300 ml. portions of water, 250 ml. saturated aqueous sodium bicarbonate solution, three 300 ml. portions of water and 200 ml. brine, dried over anhydrous sodium sulfate and concentrated in vacuo. The crude product was chromatographed on silica gel (1.5 kg), eluting with ethyl acetate/methanol (95:5). The pure product obtained was triturated with diethyl ether (150 ml) overnight to yield 14.25 g of crystalline product. Another 5.0 g of less pure product obtained from the chromatography was dissolved in 5 ml. methylene chloride and the solution was diluted with 150 ml. diethyl ether. After stirring overnight 3.42 g of crystalline product was obtained (51.5% total yield), m.p. 137°–138° C.

The NMR spectrum (250 MHz) of a deuterochloroform solution of the title compound had peaks at 0.04 (s, 3H); 0.07 (s, 3H); 0.82 (s, 9H); 1.25 (d, 3H); 2.45–2.9 (c, 2H); 3.14 (c, 1H); 3.55–4.0 (c, 3H); 4.27 (m, 1H); 5.32 (q, 2H); 5.67 and 5.7 (2d, 1H); 7.62 (d, 2H); and 8.2 (d, 2H) ppm. The infrared spectrum of a methylene chloride solution of the title compound had absorptions at 5.56, 5.92 and 6.58 microns.

The corresponding trans isomer was prepared in 25% yield using this procedure with trans-3-methylcarbonylthio-1-oxothiolane as the starting material to obtain p-nitrobenzyl (5R, 6S)- 6-[(R)-1-t-butyldimethylsilyloxyethyl]-2-[(trans)-1-oxo-3-thiolanyl]thio-2-penem-3-carboxylate. The trans isomer is less polar than the cis isomer.

The NMR spectrum (250 MHz) of a deuterochloroform solution of the corresponding trans isomer of the title compound had peaks at 0.06 (s, 3H); 0.1 (s, 3H); 0.86 (s, 9H); 1.3 (d, 3H); 2.25 (m, 1H); 2.82 (m, 1H); 2.94–3.33 (c, 3H); 3.55 (m, 1H); 3.82 (d, 1H); 4.33 (c, 1H); 4.45 (c, 1H); 5.36 (q, 2H); 5.76 (d, 1H); 7.66 (d, 2H); and 8.22 (d, 2H) ppm.

The infrared spectrum of a methylene chloride solution of the trans isomer had absorptions at 5.57, 5.92 and 6.57 microns.

PREPARATION U

Cis-3-Methylcarbonylthio-1-oxo-thiane

A solution of 300 mg. (1.04 mmole) trans 1-oxo-3-p-methyl-phenylsulfonyloxythiane and 396 mg. (1.25 mmole) tetrabutylammonium thioacetate in 20 ml. acetone was refluxed under a nitrogen atmosphere overnight. The reaction mixture was concentrated in vacuo and the residue was chromatographed on silica gel (80 g). Elution with acetone/hexane (4:1) yielded 50 mg. (25%) of the title compound.

The NMR spectrum of a deuterochloroform solution of the title compound had peaks at 1.2–3.1 (c) and 2.28 (s) (total 10H); and 3.34 (c, 2H) ppm.

Similarly, using cis-1-oxo-3-p-methylphenylsulfonyloxythiane as the starting material, trans-3-methylcarbonylthio-1-oxo-thiane was obtained in 50% yield. The NMR spectrum of a deuterochloroform solution of this trans isomer had peaks at 1.42–3.24 (c) 2.22 (s) (total 11H); and 4.06 (c, 1H) ppm.

PREPARATION V

1-Oxo-3-p-methylphenylsulfonyloxythiane p-Toluenesulfonyl chloride (3.65 g, 0.019 mole) was added to a solution of 1-oxo-3-thianol (2.14 g, 0.016 mole) and 4-dimethylaminopyridine (3.9 g, 0.032 mole) in 80 ml. methylene chloride cooled to 0° C. under nitrogen. After 30 min. at 0° C. the reaction was stirred at room temperature overnight. The solution was then washed with 50 ml. 1N aqueous hydrochloric acid solution, 50 ml. water and 50 ml. brine, dried over anhydrous sodium sulfate and concentrated in vacuo. The crude product was chromatographed on silica gel (1 kg), eluting with acetone 1 hexane (4:1) to yield 300 mg. of the trans title compound, 1.4 g. of a mixture of cis and trans title compound and 1.5 g of cis title compound (70% total yield).

The NMR spectrum of a perdeuterochloroform solution of the cis isomer of the title compound had peaks at 1.4–2.92 (c) and 2.46 (s) (total 9H); 3.4 (c, 2H); 4.54 (c, 1H); 7.36 (d, 2H); and 7.8 (d, 2H) ppm.

The NMR spectrum of a perdeuterochloroform solution of the trans isomer of the title compound had peaks at 1.4–3.3 (c) and 2.44 (s) (total 11H); 5.1 (c, 1H); 7.32 (d, 2H); and 7.77 (d, 2H) ppm.

PREPARATION W

3-Hydroxy-1-oxo-thiane m-Chloroperbenzoic acid (3.44 g, 0.017 mole, 85% pure) was added portionwise to a solution of 2.0 g (0.017 mole) thian-3-ol in 60 ml. methylene chloride cooled to 0° C. under nitrogen. The reaction mixture was stirred at 0° C. for 35 min. then at room temperature for 2 hr. It was concentrated in vacuo and the residue was chromatographed on silica gel (200 g). Elution with ethyl acetate (methanol (9:1) yielded 2.14 g (94% yield) of a mixture of cis and trans 3-hydroxy-1-oxo-thiane.

PREPARTION X

4-Methylcarbonylthiothiane

Similar procedures employed in Preparation J in reacting 3-(p-methylphenylsulfonyloxy)thiolane with potassium thioacetate by reacting 4-(p-methylphenylsulfonyloxy)thiane and 1.5 equivalents of potassium thioacetate at 80° C. in dimethylformamide to obtain 4-methylcarbonylthiothiane in 69% yield after chromatography on silica gel eluted with 10% ethyl acetate/hexane. The NMR spectrum of a deuterochloroform solution of 4-methylcarbonylthiothiane had peaks at 1.62–2.2 (4H, m); 2.32 (3H, s); 2.5–2.8 (4H, m); and 3.52 (1H, tt, J=9, 3 Hz) ppm.

PREPARATION Y

The same procedure as Preparation X was employed with trans-1-oxo-4-p-methylphenylsulfonyloxythiane as the starting material to obtain cis-1-oxo-4-(methylcarbonylthio)-thiane. The NMR spectrum (250 MHz) of a deuterochloroform solution of the product had peaks at 1.97 (2H, m); 2.33 (3H, s); 2.42 (2H, dddd); 2.66 (2H, ddd); 3.02 (2H, m); and 3.56 (1H, tt, J=11.1 3.6 Hz) ppm.

Also, the procedure of Preparation X were employed with cis-1-oxo-4-p-methylphenylsulfonyloxythiane as the starting material to obtain trans-1-oxo-4-(methylcarbonylthio)thiane. The NMR spectrum (250 MHz) of a deuterochloroform solution of the product had peaks at 1.83 (2H, m); 2.33 (3H, s); 2.65 (2H, m); 2.87 (4H, m); and 3.80 (1H, m) ppm.

PREPARATION Z trans-1-Oxo-4-p-methylphenylsulfonyloxythiane was prepared from trans-1-oxo-4-hydroxythiane (see Klein et al, Tetrahedion, 30, 2541 (1974)) according to the procedures of Preparation V using 1.5 equivalents of p-toluenesulfonyl chloride and 3 equivalents of 4-dimethylaminopyridine to obtain the desired compound as a white solid in 83% yield, m.p. 99°–102° C. The NMR spectrum (250 MHz) of a deuterochloroform solution had peaks at 1.94 (2H, m); 2.51 (3H, s); 2.6 (2H, m); 2.84 (4H, m); 4.80 (1H, m); 7.41 (2H, d, J=8 Hz); and 7.85 (2H, d, J=8 Hz) ppm.

4-p-Methylphenylsulfonyloxythiane was prepared from 4-hydroxythiane (prepared from 4-oxo-thiane by reduction with di-isobutylaluminum hydride) according to Preparation V using 1.2 equivalents of p-toluenesulfonyl chloride, 0.1 equivalents 4-dimethylaminopyridine and 1.2-equivalents triethylamine followed by silica gel column chromatography with 1:1 ethyl acetate/hexane to obtain the desired product in 95% yield. The NMR spectrum of a deuterochloroform solution of the product had peaks at 1.8–2.2 (4H, m); 2.47 (3H, s); 2.5–3.1 (4H, m); 4.60 (1H, m); 7.35 (2H, d, J=7 Hz); and 7.80 (2H, d, J=7 Hz) ppm. ·

PREPARATION AA cis-1-Oxo-3-methylcarbonylthiothiolane

A solution of trans-1-oxo-3-p-toluenesulfonyloxythiolane (25.5 g, 0.093 mole) and tetra-n-butylammonium thioacetate (59 g, 0.186 mole) in 180 ml. acetone was refluxed under nitrogen for 1.5 hr. The reaction mixture was concentrated in vacuo and the residue was chromatographed on silica gel (800 g). Elution with ethyl acetate yielded 13.4 g (81% yield) of cis-1-oxo-3-methylcarbonylthiothiolane as a solid m.p. 52.5°-54° C.

The NMR spectrum of a deuterochloroform solution of the title compound had peaks at 2.06-3.26 (c) and 2.34 (s) (total 8H); and 3.26-4.21 (c, 2H) ppm.

Similarly, trans-1-oxo-3-methylcarbonylthiothiolane was prepared from cis-1-oxo-3-p-toluenesulfonyloxythiolane in 47%, and the NMR spectrum (250 MHz) of a deuterochloroform solution of the trans isomer product had peaks at 2.1 (c, 1H); 2.36 (s, 3H); 2.9 (c, 3H); 3.17 (m, 1H); 3.36 (m, 1H); and 4.48 (m, 1H) ppm.

PREPARATION BB

1-Oxo-3-p-methylphenylsulfonyloxythiolane m-Chloroperbenzoic acid (85% pure, 1.19 g, 0.005 mole) was added portionwise over a 5 min. period to a solution of 3-p-toluenesulfonyloxythiolane (1.29 g, 0.005 mole) in 40 ml. methylene chloride cooled to 0° C. under nitrogen. After 30 min. at 0° C. the reaction mixture was diluted with 125 ml. methylene chloride and treated with 20 ml. dilute aqueous sodium bisulfite solution to destroy any excess peracid. The pH of the mixture was adjusted to 7.5 with sodium bicarbonate and the methylene chloride layer was washed with 20 ml. water and 20 ml. brine, dried over anhydrous sodium sulfate and concentrated in vacuo. The residue was chromaotgraphed on silica gel (200 g) eluting with 95:5 ethyl acetate/methanol to yield 0.175 g of the more polar cis isomer and 0.92 g of the less polar trans isomer as oils (80% yield) which solidified. M.P. of trans isomer 85°-87° C., the cis isomer is a low melting waxy solid.

The NMR spectrum of a deuterochloroform solution of the trans isomer of the title compound had peaks at 2.2-3.63 (c) and 2.5 (s) (total 9H); 5.42 (m, 1H); 7.34 (d, 2H); and 7.78 (d, 2H) ppm.

The NMR spectrum of a deuterochloroform solution of the cis isomer of the title compound had peaks at 1.95-3.23 (c) and 2.46 (s) (total 9H); 5.2 (c, 1H); 7.3 (d, 2H); and 7.76 (d, 2H) ppm.

PREPARATION CC

3-p-Methylphenylsulfonyloxythiolane p-Toluenesulfonyl chloride (0.95 g, 0.005 mole) was added to a solution of thiolan-3-ol (0.52 g, 0.005 mole) and 4-dimethylaminopyridine (1.22 g, 0.01 mole) in 20 ml. methylene chloride cooled to 0° C. under nitrogen. After stirring 1.5 hr. at 0° C. the reaction was allowed to warm to room temperature. After 4 hr. at room temperature the reaction was complete. The reaction mixture was diluted with 80 ml. methylene chloride and washed with 20 ml. dilute aqueous hydrochloric acid solution, 20 ml. water and 20 ml. brine. The organic layer was dried over anhydrous sodium sulfate and concentrated in vacuo to an oil which solidified on standing (1.3 g, 100% yield), m.p. 56.5°-58° C.

The NMR spectrum of a perdeuterodichloromethane solution of the title compound had peaks at 1.5-2.52 (c) and 2.44 (s) (total 5H); 2.56-3.02 (c, 4H); 5.13 (m, 1H); 7.28 (d, 2H); and 7.72 (d, 2H) ppm.

I claim:
1. A compound of the formula

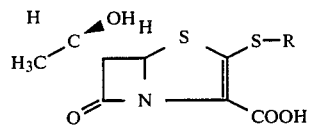

or a pharmaceutically-acceptable salt thereof, wherein:
R is trans-1-oxo-3-thiolanyl, cis-1-oxo-3-thiolanyl, 1,1-dioxo-3-thiolanyl, trans-1-oxo-3-thianyl, cis-1-oxo-3-thianyl, trans-1-oxo-3-thiethanyl, 1,1-dioxo-4-thianyl, 4-thianyl, trans-1-oxo-4-thianyl, cis-1-oxo-4-thianyl, cis-1-oxo-3-thietanyl or 1-oxo-3-thiolanyl.

2. A compound according to claim 1 wherein R is trans-1-oxo-3-thiolanyl.
3. A compound according to claim 1 wherein R is cis-1-oxo-3-thiolanyl.
4. A compound according to claim 1 wherein R is 1,1-dioxo-3-thiolanyl.
5. A compound according to claim 1 wherein R is trans-1-oxo-3-thianyl.
6. A compound according to claim 1 wherein R is cis-1-oxo-3-thianyl.
7. A compound according to claim 1 wherein R is trans-1-oxo-3-thietanyl.
8. A compound according to claim 1 wherein R is 1,1-dioxo-4-thianyl.
9. A compound according to claim 1 wherein R is 4-thianyl.
10. A compound according to claim 1 wherein R is trans-1-oxo-4-thianyl.
11. A compound according to claim 1 wherein R is cis-1-oxo-4-thianyl.
12. A compound according to claim 1 wherein R is cis-1-oxo-3-thietanyl.
13. A compound according to claim 1 wherein R is 1-oxo-3-thiolanyl.
14. A compound of the formula

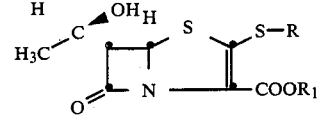

wherein
$R_1$ is (2-methyl-2-propylcarbonyloxy)methyl, phthalidyl, (5-methyl-2-oxo-1,3-dioxolen-4-yl)methyl, 1-(methylcarbonyloxy)-1-ethyl or 1-(ethoxycarbonyloxy)-1-ethyl;
and R is 1-oxo-3-thiolanyl or cis-1-oxo-3-thiolanyl.
15. A compound according to claim 14 wherein R is 1-oxo-3-thiolanyl.
16. A compound according to claim 14 wherein R is cis-1-oxo-3-thiolanyl.
17. An antibacterial pharmaceutical composition comprising a penem compound according to claim 1 and a pharmaceutically acceptable carrier;
wherein the ratio of the pharmaceutically acceptable carrier to the penem compound is in the range from 1:10 to 4:1.
18. A method of treating a bacterial infection in a mammal comprising administering an antibacterially effective amount of a compound according to claim 1.
19. A compound according to claim 16, wherein $R_1$ is (2-methyl-2-propylcarbonyloxy)methyl.

20. (2-Methyl-2-propylcarbonyloxy)methyl (5R,6S)-6-((R)-1-hydroxyethyl)-2-(1,1-dioxo-3-thiolanyl)thio-2-penem-3-carboxylate.

21. An antibacterial pharmaceutical composition comprising a penem compound according to claim 14 and a pharmaceutically-acceptable carrier;
    wherein the ratio of the pharmaceutically acceptable carrier to the penem compound is in the range from 1:10 to 4:1.

22. A method of treating a bacterial infection in a mammal comprising administering an antibacterially effective amount of a compound according to claim 14.

23. An antibacterial pharmaceutical composition comprising a penem compound according to claim 20 and a pharmaceutically-acceptable carrier;
    wherein the ratio of the pharmaceutically acceptable carrier to the penem compound is in the range from 1:10 to 4:1.

24. A method of treating a bacterial infection in a mammal comprising administering an antibacterially effective amount of a compound according to claim 20.

* * * * *